(12) United States Patent
Konishi et al.

(10) Patent No.: US 9,056,309 B2
(45) Date of Patent: Jun. 16, 2015

(54) METHOD FOR PREPARING RUTHENIUM CATALYST FOR PRODUCING CYCLOOLEFIN AND METHOD AND APPARATUS FOR PRODUCING CYCLOOLEFIN

(75) Inventors: Mitsuo Konishi, Tokyo (JP); Masakazu Sato, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 275 days.

(21) Appl. No.: 13/141,146

(22) PCT Filed: Nov. 19, 2009

(86) PCT No.: PCT/JP2009/006249
§ 371 (c)(1),
(2), (4) Date: Jun. 21, 2011

(87) PCT Pub. No.: WO2010/073481
PCT Pub. Date: Jul. 1, 2010

(65) Prior Publication Data
US 2011/0257449 A1 Oct. 20, 2011

(30) Foreign Application Priority Data
Dec. 22, 2008 (JP) .................. 2008-325644

(51) Int. Cl.
*B01J 37/16* (2006.01)
*B01J 37/18* (2006.01)
(Continued)

(52) U.S. Cl.
CPC ............ *B01J 23/60* (2013.01); *B01J 21/066* (2013.01); *B01J 23/462* (2013.01);
(Continued)

(58) Field of Classification Search
CPC ............ B01J 37/18; B01J 37/08; B01J 23/60; B01J 23/652; B01J 23/89; B01J 23/46; C07C 5/11; C07C 13/20; C07B 61/00
USPC ........... 585/251; 502/100, 325, 326, 328, 329
See application file for complete search history.

(56) References Cited

U.S. PATENT DOCUMENTS 4,734,536 A 3/1988 Nagahara et al.
5,969,202 A 10/1999 Ashida et al.
(Continued)

FOREIGN PATENT DOCUMENTS

CA 2055444 4/1999
EP 0 659 718 A1 6/1995
(Continued)

OTHER PUBLICATIONS

Supplementary European Search Report for EP Application No. 09634297.5 dated Nov. 21, 2012.
(Continued)

*Primary Examiner* — In Suk Bullock
*Assistant Examiner* — Philip Louie
(74) *Attorney, Agent, or Firm* — Finnegan, Henderson, Farabow, Garrett & Dunner, LLP

(57) ABSTRACT

A method for preparing a ruthenium catalyst, including a step of reducing a ruthenium catalyst precursor by holding the ruthenium catalyst precursor in an aqueous solution containing a metal salt at a temperature within the range of more than 180° C. and 220° C. or less and a hydrogen partial pressure within the range of 0.6 MPa or more and 5 MPa or less. A method for producing a cycloolefin, including a step of preparing a ruthenium catalyst by the method including a step of reducing a ruthenium catalyst precursor in an aqueous solution containing a metal salt by holding the ruthenium catalyst precursor at a temperature within the range of more than 180° C. and 220° C. or less and a hydrogen partial pressure within the range of 0.6 MPa or more and 5 MPa or less, and a step of partially hydrogenating a monocyclic aromatic hydrocarbon by use of the ruthenium catalyst obtained.

3 Claims, 2 Drawing Sheets

(51) Int. Cl.
*C07C 5/11* (2006.01)
*B01J 23/60* (2006.01)
*B01J 23/46* (2006.01)
*B01J 23/652* (2006.01)
*B01J 23/89* (2006.01)
*B01J 35/00* (2006.01)
*B01J 37/03* (2006.01)
*B01J 37/14* (2006.01)
*B01J 21/06* (2006.01)

(52) U.S. Cl.
CPC ......... *B01J 23/6522* (2013.01); *B01J 23/8913* (2013.01); *B01J 23/8953* (2013.01); *B01J 35/006* (2013.01); *B01J 37/031* (2013.01); *B01J 37/14* (2013.01); *B01J 37/18* (2013.01); *C07C 5/11* (2013.01); *C07C 2101/16* (2013.01); *C07C 2523/46* (2013.01)

(56) References Cited

U.S. PATENT DOCUMENTS

| | | | |
|---|---|---|---|
| 5,973,218 A | * | 10/1999 | Ashida et al. ................. 585/273 |
| 6,077,983 A | | 6/2000 | Ono et al. |
| 2004/0157938 A1 | * | 8/2004 | Iwamoto et al. ............. 518/716 |
| 2011/0130600 A1 | | 6/2011 | Konishi |

FOREIGN PATENT DOCUMENTS

| | | | |
|---|---|---|---|
| EP | 1 767 270 A1 | | 3/2007 |
| JP | 63-243038 | | 10/1988 |
| JP | 9-104643 | | 4/1997 |
| JP | 2634828 | | 4/1997 |
| JP | 2886563 | | 2/1999 |
| JP | 11-226401 | | 8/1999 |
| JP | 11226401 | * | 8/1999 |
| JP | 3141944 | | 12/2000 |
| WO | WO-97/16249 | | 5/1997 |
| WO | WO 2010/013548 A1 | | 2/2010 |

OTHER PUBLICATIONS

International Search Report from the Japanese Patent Office for International Application No. PCT/JP2009/006249 (Mail date Feb. 16, 2010).

* cited by examiner

METHOD FOR PREPARING RUTHENIUM CATALYST FOR PRODUCING CYCLOOLEFIN AND METHOD AND APPARATUS FOR PRODUCING CYCLOOLEFIN

TECHNICAL FIELD

The present invention relates to a method for preparing a ruthenium catalyst for producing a cycloolefin by subjecting a monocyclic aromatic hydrocarbon to a partial hydrogenation reaction, a method for producing a cycloolefin using the ruthenium catalyst and an apparatus for realizing the method.

BACKGROUND ART

Various methods have been conventionally known for producing a cycloolefin. As one of the methods, a method of subjecting a monocyclic aromatic hydrocarbon to partial hydrogenation performed in a liquid phase using a ruthenium catalyst is known. In producing a cycloolefin by partial hydrogenation of a monocyclic aromatic hydrocarbon, a catalyst component, a type of carrier, a metal salt as an additive to a reaction system, and the like have been investigated in order to improve selectivity of a cyclohexene or yield and the results thereof have been reported in many documents.

For example, a method (Patent Literature 1) for producing a cycloolefin is known, in which a reaction is performed by using a hydrogenation catalyst particle containing a ruthenium metal having an average crystallite diameter of 20 nm or less and adding at least one compound selected from an oxide, a hydroxide and a hydrate of Zr, Hf, Ti, Nb, Ta, Cr, Fe, Co, Al, Ga and Si besides the catalyst particle, further in the copresence of at least one type of zinc compound serving as a co-catalyst and under neutral or acidic conditions. Furthermore, for example, a catalyst for producing a cycloolefin (Patent Literature 2) is known, which is a catalyst employing zirconia as a carrier and formed of particles having an average particle size of a primary particle within the range of 3 to 50 nm and a secondary particle size within the range of 0.1 to 30 μm.

In addition, a pretreatment method (Patent Literature 3) for a ruthenium catalyst is proposed for separating an aqueous phase consisting of a ruthenium catalyst and water from a reaction product without fail. In the method, the aqueous phase containing a ruthenium catalyst is held while stirring at a temperature of 60 to 180° C. in a predetermined time in the absence of an oil-phase component such as a raw-material aromatic hydrocarbon.

Meanwhile, a method of regenerating a ruthenium catalyst reduced in activity by the interaction between hydrogen and the ruthenium catalyst is proposed (Patent Literature 4). In this method, the ruthenium catalyst is brought into contact with oxygen in a liquid phase.

Furthermore, an activity recovery method for a ruthenium catalyst is proposed (Patent Literature 5). In this method, a ruthenium catalyst used in a hydrogenation reaction of an unsaturated organic compound and reduced in activity is held at a hydrogen partial pressure, which is lower than the hydrogen partial pressure of the hydrogenation reaction conditions, and at a temperature not less than the temperature of the hydrogenation reaction minus 50° C. and not more than 250° C.

Moreover, an activity recovery method for a ruthenium catalyst is proposed (Patent Literature 6). This method includes a step of bringing a ruthenium catalyst into contact with oxygen in a liquid phase and a step of holding the catalyst at a hydrogen partial pressure lower than the hydrogen partial pressure in the hydrogenation reaction and at a temperature not less than the temperature of the hydrogenation reaction temperature minus 50° C.

CITATION LIST

Patent Literature

Patent Literature 1: U.S. Pat. No. 4,734,536
Patent Literature 2: European Patent Application Laid-Open No. 1767270
Patent Literature 3: Japanese Patent No. 3141944
Patent Literature 4: Japanese Patent No. 2634828
Patent Literature 5: Japanese Patent No. 2886563
Patent Literature 6: International Publication No. WO 97/16249

SUMMARY OF INVENTION

Technical Problem

It is known that, in the partial hydrogenation reaction of a monocyclic aromatic hydrocarbon, as the conversion rate of a raw-material monocyclic aromatic hydrocarbon increases, the selectivity of a desired cycloolefin generally decreases, and that the yield of a cycloolefin, which is a product obtained by multiplying the conversion rate of a monocyclic aromatic hydrocarbon by the selectivity of a cycloolefin, has a maximum value relative to the conversion rate of the monocyclic aromatic hydrocarbon. Accordingly, in the oil phase obtained after partial hydrogenation of the monocyclic aromatic hydrocarbon, not only a cycloolefin but also a raw-material monocyclic aromatic hydrocarbon as well as completely hydrogenated saturated monocyclic hydrocarbon come to remain. If the partial hydrogenation is terminated at the stage where the selectivity of a cycloolefin is still high (the conversion rate of a monocyclic aromatic hydrocarbon is low), the amount of by-product, i.e., a saturated monocyclic hydrocarbon, can be reduced. However, a raw-material monocyclic aromatic hydrocarbon, a desired cycloolefin and a by-product, i.e., saturated monocyclic hydrocarbon have similar boiling points. In this case, since a large amount of monocyclic aromatic hydrocarbon must be separated, much energy is required for obtaining a cycloolefin by separation and purification. In the case where the reaction is terminated at a conversion rate of a monocyclic aromatic hydrocarbon at which a maximum yield of a cycloolefin is obtained and a cycloolefin is separated and purified from the oil phase thus obtained, if the selectivity of a cycloolefin is low, a lot of energy is required for separating a by-product, i.e., a saturated monocyclic hydrocarbon from a raw-material aromatic hydrocarbon. Accordingly, to reduce the amount of by-product, a saturated monocyclic hydrocarbon, and also reduce separation and purification energy, it is necessary to obtain a highest possible selectivity of a cycloolefin at a highest possible conversion rate of a monocyclic aromatic hydrocarbon. In short, it is desired to develop a catalyst and a production method providing a cycloolefin in higher yield. In view of this, the yields of a cycloolefin of the conventional methods disclosed in the aforementioned patent literatures are still insufficient. It is therefore desired, to develop a catalyst and method for producing a cycloolefin capable of providing a further higher yield of a cycloolefin in a partial hydrogenation reaction and if a conversion rate is the same, a further higher selectivity of a cycloolefin, stably for a long time, A pretreatment method and an activity recovery method for a catalyst disclosed in the above patent literatures are useful in order to recover the activity; however, they are still unsatisfactory in view of cycloolefin yield by partial hydrogenation.

The present invention was made in the aforementioned circumstances and is directed to providing a method for preparing a ruthenium catalyst capable of tremendously enhancing yield compared to conventional methods, a production method for a cycloolefin capable of producing a cycloolefin in high yield stably for a long time by using the catalyst and a production apparatus for realizing the production method.

Solution to Problem

In the aforementioned circumstances, the present inventors conducted various studies on a method for preparing a ruthenium catalyst for improving the yield of a cycloolefin. As a result, they surprisingly found that the yield of a cycloolefin can be tremendously improved by partially hydrogenating a monocyclic aromatic hydrocarbon using a ruthenium catalyst obtained by reducing a ruthenium catalyst precursor by holding it at a temperature within a range of more than 180° C. and 220° C. or less and at a hydrogen partial pressure within a range of 0.6 MPa or more and 5 MPa or less, in an aqueous solution containing a metal salt.

They further found that the selectivity of a cycloolefin can be improved and a cycloolefin can be produced in high yield for a long time by a method for producing a cycloolefin by subjecting a monocyclic aromatic hydrocarbon to a partial hydrogenation reaction in an aqueous phase containing a ruthenium catalyst and/or a ruthenium catalyst precursor, an aqueous solution containing a metal salt. The method includes a first step of bringing at least part of the ruthenium catalyst contained in the aqueous phase into contact with oxygen and a second step of reducing at least part of the aqueous phase containing the ruthenium catalyst obtained through the first step by holding the aqueous phase at a temperature within a range of more than 180° C. and 220° C. or less and at a hydrogen partial pressure within a range of 0.6 MPa or more and 5 MPa or less. Based on the findings, the present invention was accomplished.

More specifically, the present invention is as described below.

[1]
A method for preparing a ruthenium catalyst, comprising a step of reducing a ruthenium catalyst precursor by holding the ruthenium catalyst precursor in an aqueous solution containing a metal salt at a temperature within a range of more than 180° C. and 220° C. or less and at a hydrogen partial pressure within a range of 0.6 MPa or more and 5 MPa or less.

[2]
A method for producing a cycloolefin, comprising a step of preparing a ruthenium catalyst by the method according to the above [1] and partially hydrogenating a monocyclic aromatic hydrocarbon by use of the ruthenium catalyst obtained.

[3]
A method for producing a cycloolefin, comprising
a first step of producing a cycloolefin by the method according to the above [2] and thereafter bringing the ruthenium catalyst into contact with oxygen, and
a second step of reducing at least part of an aqueous phase containing the ruthenium catalyst obtained through the first step by holding the aqueous phase at a temperature within a range of more than 180° C. and 220° C. or less and at a hydrogen partial pressure within a range of 0.6 MPa or more and 5 MPa or less.

[4]
A method for producing a cycloolefin by subjecting a monocyclic aromatic hydrocarbon to a partial hydrogenation reaction in an aqueous phase containing a ruthenium catalyst and/or a ruthenium catalyst precursor, an aqueous solution containing a metal salt, the method comprising:
a first step of bringing at least part of the ruthenium catalyst contained in the aqueous phase into contact with oxygen; and
a second step of reducing at least part of an aqueous phase containing the ruthenium catalyst obtained through the first step by holding the aqueous phase at a temperature within a range of more than 180° C. and 220° C. or less, and at a hydrogen partial pressure within a range of 0.6 MPa or more and 5 MPa or less.

[5]
An apparatus for producing a cycloolefin, having
a reactor storing an aqueous phase containing a ruthenium catalyst and an aqueous solution containing a metal salt,
an oil/water separation vessel connected to the reactor,
an oxygen treater connected to the oil/water separation vessel, and
a hydrogen treater connected to the oxygen treater,
wherein a monocyclic aromatic hydrocarbon is supplied to the reactor, at least part of the reaction solution and at least part of an aqueous phase containing the ruthenium catalyst is supplied to the oil/water separation vessel and the aqueous phase discharged from the oil/water separation vessel is introduced into the oxygen treater and brought into contact with oxygen, and thereafter introduced into the hydrogen treater.

Advantageous Effects of Invention

By virtue of the production method of the present invention it is possible to obtain a cycloolefin with high selectivity and in high yield stably for a long time by a partial hydrogenation reaction of a monocyclic aromatic hydrocarbon.

DESCRIPTION OF EMBODIMENT

Figure 1:
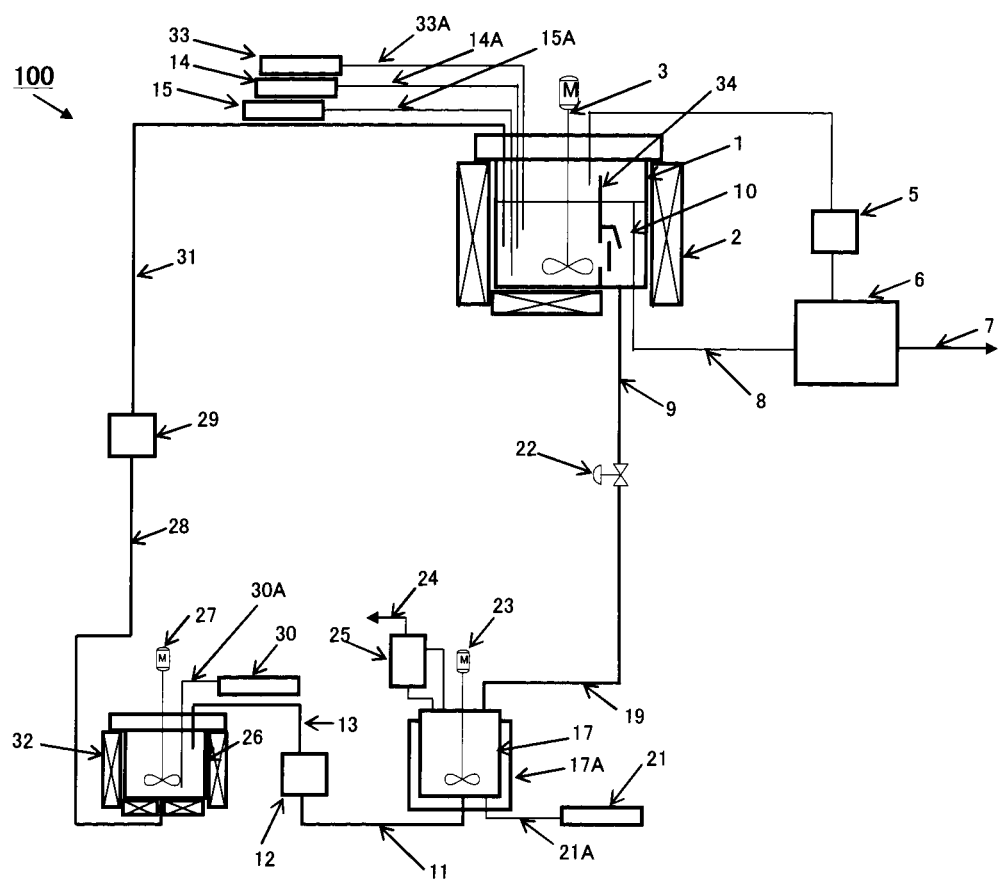
FIG. 1 is a schematic view showing an embodiment of a cycloolefin production apparatus of the present invention.

An embodiment of the present invention (hereinafter referred to simply as "the embodiment") will be described below, if necessary, referring to drawings. However, the present invention is not limited to the following embodiments. The present invention may be modified in various ways without departing from the scope of the invention. Note that like reference numerals are used to designate like elements in the drawings and any further explanation is omitted for brevity's sake. Furthermore, the dimensional ratios of the drawings are not limited to those shown in the figures.

[1] Method for Preparing a Ruthenium Catalyst

A method for preparing a ruthenium catalyst according to the embodiment includes a step of holding the ruthenium catalyst precursor in an aqueous solution containing a metal salt at a temperature within a range of more than 180° C. and 220° C. or less and at a hydrogen partial pressure within a range of 0.6 MPa or more and 5 MPa or less.

The ruthenium catalyst of the embodiment preferably contains a ruthenium metal obtained by reducing any one of various ruthenium compounds. Examples of the ruthenium compound include halides such as a chloride, a bromide and an iodide, nitrates, sulfates, hydroxides of ruthenium, various types of complexes containing ruthenium and compounds derived from these complexes. Examples of the complex containing ruthenium include a ruthenium carbonyl complex, a ruthenium acetylacetonato complex, a ruthenocene complex, a ruthenium amine complex and a ruthenium hydride complex. These ruthenium compounds can be used alone or in combination with two types or more.

In the embodiment, a ruthenium catalyst can be obtained by reducing a ruthenium compound as mentioned above in an aqueous solution containing a metal salt at a temperature within a range of more than 180° C. and 220° C. or less and at a hydrogen partial pressure within a range of 0.6 MPa or more and 5 MPa or less. Alternatively, a ruthenium catalyst can be obtained by reducing a ruthenium compound previously (before the reducing treatment performed in the aforementioned conditions) in the following customary method and thereafter reducing the ruthenium catalyst with hydrogen in the reduction conditions of the embodiment. If the ruthenium compound reduced in the customary conditions is further reduced in the conditions of the embodiment, the effect of enhancing cycloolefin selectivity tends to be further increased. For the reason, more preferably, the latter method is employed.

Examples of the customary method for reducing a ruthenium compound include a catalytic reduction method by e.g., hydrogen or carbon monoxide and a chemical reduction method by e.g., formalin, sodium borohydride, potassium borohydride, hydrazine, ascorbic acid or an alcohol. Of them, preferable reduction methods are a catalytic reduction method by hydrogen and a chemical reduction method by sodium borohydride. In the case of the catalytic reduction method by hydrogen, reduction activation of a ruthenium compound is performed at a reduction temperature of usually 50 to 450° C. and preferably 100 to 400° C. When the reduction temperature is less than 50° C., reduction tends to require excessively long time. In contrast, when the reduction temperature exceeds 450° C., aggregation of ruthenium proceeds, tends to have an adverse effect upon the activity and selectivity of a ruthenium catalyst. Note that reduction of a ruthenium compound may be performed in a gaseous phase or a liquid phase; however, preferably, a liquid phase reduction is employed. Furthermore, in the case of a chemical reduction method by e.g., formalin, sodium borohydride or hydrazine, the reduction temperature is preferably 100° C. or less and more preferably, 10° C. to 60° C.

The ruthenium compound (hereinafter, referred to also as "ruthenium catalyst precursor") reduced or not reduced by a customary method, is reduced in an aqueous solution containing a metal salt at a temperature within the range of more than 180° C. and 220° C. or less and at a hydrogen partial pressure within the range of 0.6 MPa or more and 5 MPa or less. If the hydrogen partial pressure is less than 0.6 MPa or the temperature is 180° C. or less, no improvement of cycloolefin selectivity is seen, with the result that the yield of a cycloolefin cannot be improved. Furthermore, if the hydrogen partial pressure exceeds 5 MPa or the temperature exceeds 220° C., partial hydrogenation reaction activity of a ruthenium catalyst decreases, with the result that an industrially satisfactory reaction rate cannot be obtained and a large amount of ruthenium catalyst must be used. More preferable hydrogen partial pressure is within the range of 1 MPa or more and 4 MPa or less and more preferable temperature is within the range of 185° C. or more and 210° C. or less.

In the method for preparing a ruthenium catalyst of the embodiment, it is necessary to reduce a ruthenium catalyst precursor in an aqueous solution containing a metal salt. The metal salt used herein is preferably present in the state where at least a part or whole thereof is dissolved in an aqueous phase. Examples of a metal constituting the metal salt include zinc, iron, cadmium, gallium, indium, aluminium, chromium, manganese, cobalt and copper. Furthermore, examples of the metal salt include a nitrate, acetate, phosphate and sulfate of a metal as mentioned above. A double salt containing such metal salts may be used. These metal salts may be used alone or in combination with two or more types. In view of improving a selectivity of a cycloolefin of the ruthenium catalyst obtained, zinc sulfate is particularly preferably used as a metal salt.

Furthermore, besides those as mentioned above, the following metal salts may be present in an aqueous solution for a reduction treatment. Examples of a metal constituting such a metal salt include metals of the 1st family such as lithium, sodium and potassium and metals of the 2nd family such as magnesium and calcium according to the periodic table (the family number follows the IUPAC inorganic chemical nomenclature, revised version (1989)) and lead, arsenic, germanium, vanadium, silver, gold, platinum, palladium, barium and boron. Furthermore, examples of the metal salt include a nitrate, an oxide, a hydroxide, an acetate, a phosphate and a chemical and/or physical mixture of two or more salts of these.

The concentration of each of these metal salts in the aqueous phase in a reductive reaction is preferably $1 \times 10^{-5}$ to 5.0 mol/L. If a metal salt containing zinc sulfate is used, the metal salt concentration in the aqueous phase is more preferably $1 \times 10^{-3}$ to 2.0 mol/L and further preferably 0.1 to 1.0 mol/L. Furthermore, the amount of metal salt is preferably $1 \times 10^{-5}$ to $1 \times 10^5$ times by mass relative to the amount of ruthenium in a ruthenium catalyst. It is not necessary for each of these metal salts to be entirely dissolved in an aqueous phase and part of the metal may precipitate in an aqueous phase.

In view of improving the cycloolefin selectivity of a ruthenium catalyst, the aqueous solution of a metal salt contained in the aqueous phase preferably has a pH of 7.5 or less, more preferably 1.0 to 7.0 and further preferably 1.5 to 6.5 (in the acidic region). If the aqueous solution of a metal salt is alkaline, the stability of a metal salt in a reductive reaction reduces and a metal salt precipitates on a ruthenium catalyst and the activity of the catalyst may decrease. This case is not preferable. To maintain the aqueous phase to be neutral or acidic, for example, an acidic component such as nitric acid, sulfuric acid, acetic acid and phosphoric acid may be contained in an aqueous solution.

The time for the reduction treatment is preferably 5 minutes to about one week. If the time is less than 5 minutes, the effect of improving cycloolefin selectivity by a reduction treatment under the conditions of the embodiment tends to decrease. In contrast, if the reduction time is extremely long, the resultant activity of the ruthenium catalyst tends to decrease. The time of the reduction treatment is more preferably 10 minutes to 100 hours.

As an instrument for the reduction treatment, a stirring/mixing vessel can be used and an immobilized bed can be used. If a stirring/mixing vessel is used, a ruthenium catalyst precursor is dispersed in an aqueous solution containing a metal salt to obtain a catalyst precursor slurry and thereafter, a reduction treatment is performed while stirring under a hydrogen atmosphere at a predetermined temperature and pressure. To raise the dissolution rate of hydrogen into an aqueous solution to thereby uniformly reduce a ruthenium catalyst precursor, a hydrogen blowing-in pipe is provided and a reduction treatment is preferably performed while vigorously stirring. Furthermore, if a ruthenium catalyst precursor is in the form of e.g., particles and desired to maintain the form as they are, for example, an immobilized bed is filled with the ruthenium catalyst precursor and an aqueous solution containing a metal salt and hydrogen are supplied through the bed at a predetermined temperature and at a hydrogen partial pressure to perform a reduction treatment.

The ruthenium catalyst obtained in the reduction treatment conditions of the embodiment can be directly used in the partial hydrogenation reaction of a monocyclic aromatic hydrocarbon in the aqueous solution of a metal salt used in the reduction treatment. Furthermore, the ruthenium catalyst obtained after the reduction treatment is separated from the aqueous solution of a metal salt and thereafter can be used in partial hydrogenation of a monocyclic aromatic hydrocarbon. If the ruthenium catalyst obtained in the reduction treatment of the embodiment is stored at normal temperature and in the air after the reduction treatment, the catalyst is preferably used within a month, more preferably within a week in the partial hydrogenation reaction of a monocyclic aromatic hydrocarbon, particularly preferably within several hours. In the case where the catalyst is stored for more than one month, a cycloolefin selectivity improving effect tends to be rarely obtained. If the catalyst must be stored for a long time, it is preferably stored in an inert gas such as nitrogen and argon or in hydrogen under normal pressure or pressurized conditions.

The ruthenium catalyst may be obtained by supplying a ruthenium catalyst precursor to a partial hydrogenation reactor and thereafter applying a reduction treatment to the precursor under conditions specified by the embodiment or by supplying a ruthenium catalyst precursor to a reactor and thereafter applying a reduction treatment under the customary conditions and further applying a reduction treatment under the conditions specified by the embodiment. Alternatively, a ruthenium catalyst precursor is reduced in the customary conditions and supplied to a partial hydrogenation reactor and then may be reduced in the conditions specified by the embodiment.

A ruthenium catalyst precursor containing no ruthenium metal is preferably used in the form of a ruthenium hydroxide supported body, which is obtained by fitting a ruthenium compound specifically described above onto a carrier and treating the compound with an alkali such as sodium hydroxide. Alternatively, a ruthenium catalyst precursor is preferably a mixture of ruthenium hydroxide and a dispersant obtained by adding an alkali such as sodium hydroxide to a mixture in which a dispersant and a ruthenium compound as described above are present, or a mixture of a dispersant and a ruthenium hydroxide obtained by adding an alkali such as sodium hydroxide to a ruthenium compound as described above. The ruthenium compound sometimes contains an anion such as a chlorine ion, which may accelerate corrosion of a material; however, if a ruthenium compound is treated with alkali and then washed with e.g., water, it is possible to prevent such an anion from entering a reaction system. Thus after the alkali treatment, washing is preferably performed.

The ruthenium catalyst may be obtained, before, during or after reduction of a ruthenium compound, by adding another metal and/or a metal compound, for example, zinc, chromium, molybdenum, tungsten, manganese, cobalt, iron, copper, gold, platinum, boron, lanthanum, cerium, and/or a compound thereof, to the ruthenium compound. In the case where a metal and/or a metal compound is added, usually, the amount of metal and/or metal compound preferably falls within the range of 0.001 to 20 in terms of atomic ratio relative to a ruthenium atom. Of the metals and the metal compounds, zinc and/or a zinc compound are preferable. The zinc and/or zinc compound is preferably added before or during reduction of a ruthenium compound. The addition amount of zinc and/or zinc compound is preferably 0.1 to 50 parts by mass in terms of zinc relative to 100 parts by mass of ruthenium. Furthermore, in view of catalytic activity and cycloolefin selectivity, the amount is preferably 0.5 to 30 parts by mass in terms of zinc relative to 100 parts by mass of ruthenium. If the amount of zinc is 0.1 part by mass or more relative to 100 parts by mass of ruthenium, the yield of a cycloolefin tends to be high. If the amount of zinc is 50 parts by mass or less, catalytic activity tends to be high.

As a ruthenium catalyst precursor containing ruthenium as a main component and the above metal and/or metal compound, for example, the following (1) to (4) are mentioned.

(1) A ruthenium compound and another metal and/or metal compound supported on a carrier by a general carrying method such as an adsorption method, an ion exchange method, an impregnating method, a coprecipitation method and solidification by drying.

(2) An insoluble salt formed of a ruthenium compound and another metal and/or a metal compound by adding an alkali such as sodium hydroxide to a solution containing a ruthenium compound and another metal and/or a metal compound.

(3) an aqueous solution containing a ruthenium compound, if necessary, supported on a carrier, and another metal compound which is converted into a solid by a reduction treatment.

(4) a liquid phase in which a ruthenium compound is dissolved together with another metal compound.

As mentioned above, a ruthenium catalyst may be a supported body having ruthenium supported on a carrier. A carrier is not particularly limited as long as it can support general ruthenium catalysts. Specific examples of the carrier include an oxide, complex oxide, hydroxide and poorly water-soluble metal salt of a metal such as magnesium, aluminium, silicon, calcium, titanium, vanadium, chromium, manganese, cobalt, iron, copper, zinc, zirconium, hafnium, tungsten, boron, lanthanum and cerium. Alternatively, a compound obtained by chemically or physically combining these two types or more compounds and a mixture thereof may be included.

Of them, as the carrier, zirconium oxide (zirconia) and/or zirconium hydroxide are preferable; in particular, zirconium oxide is preferable since it tends to have an excellent physical stability of the specific surface area or the like under reaction conditions. Zirconium oxide preferably has an average particle size of 0.05 to 30 μm and more preferably 0.05 to 10 μm. Furthermore, in order to support ruthenium in a highly dispersed state to enhance catalytic activity of ruthenium per unit amount, the specific surface area of zirconium oxide is preferably 20 to 200 $m^2/g$. Examples of the method for supporting ruthenium onto a carrier include, but not particularly limited to, an adsorption method, an ion exchange method, an impregnating method, a coprecipitation method and solidification by drying.

Note that an average particle size herein is obtained by measuring a particle-size distribution (ratio of particles within a predetermined particle-size range) by a laser diffraction light-scattering particle size analyzer (for example, product name "MT3000" produced by Microtrac Inc.), obtaining a cumulative particle-size distribution by regarding its whole volume as 1000, and defining a particle size at a 50% cumulative point. In short, the average particle size refers to a cumulative average diameter (central diameter, median diameter). Furthermore, the specific surface area is obtained from desorption data based on measurement by a BET method using nitrogen as an adsorption gas. Measurement of a specific surface area by the BET method can be performed by, for example, Micrometrics ASAP2010 produced by Shimadzu Corporation.

The use amount of carrier is not particularly limited; however, in general, it is preferably 1 to 1000 times by mass standard as large as ruthenium to be supported thereon. Particularly, in the case where zirconium oxide is used as a carrier, zirconium oxide is more preferably used in an amount 1 to 200 times (by mass standard) and further preferably 2 to 10 times as large as ruthenium to be supported thereon. A catalyst supporting ruthenium in a highly dispersed state, which is about 1 to 200 times as large as by mass standard, tends to have good catalytic activity per unit amount of ruthenium.

Furthermore, to enhance selectivity of a cycloolefin, it is preferred to allow a dispersant to be present in catalyst slurry. The dispersant may be contained in a ruthenium catalyst by physical mixing regardless of whether ruthenium is supported or not supported thereon. Examples of the dispersant include an oxide, complex oxide, hydroxide and poorly water-soluble metal salt of a metal such as magnesium, aluminium, silicon, calcium, titanium, vanadium, chromium, manganese, cobalt, iron, copper, zinc, zirconium, hafnium, tungsten, barium and boron. Alternatively, a compound obtained by chemically or physically combining two types or more compounds of these and a mixture thereof may be included. Of them, as the dispersant, zirconium oxide and zirconium hydroxide are preferable. In particular, zirconium oxide is preferable since it tends to enhance selectivity of a cycloolefin and have an excellent physical stability of the specific surface area or the like under reaction conditions. Note that the "catalyst slurry" refers to an aqueous phase containing an aqueous solution containing a metal salt and a ruthenium catalyst obtained by a preparation method of the embodiment.

The use amount of dispersant is not particularly limited; however it is preferably 1 to 1000 times by mass standard as large as ruthenium to be used in a catalyst. Particularly, in the case where zirconium oxide is used as a dispersant, zirconium oxide is more preferably used in an amount of 1 to 200 times by mass standard as large as ruthenium and further preferably, in an amount of 2 to 40 times. Use of a dispersant within the range above can lower a risk of reducing catalytic activity caused by the aggregation of a ruthenium catalyst in a reaction system.

The average crystallite diameter of a ruthenium catalyst is preferably 20 nm or less. If the average crystallite diameter falls within the range, the surface area of the ruthenium catalyst appropriately increases and a sufficient number of active centers are present, with the result that a catalytic activity tends to improve. The average crystallite diameter of a ruthenium catalyst is calculated in accordance with the Scherrer equation based on the broadening of the width of the diffraction line obtained by an X-ray diffraction analysis of the ruthenium catalyst. More specifically, the average crystallite diameter of a ruthenium catalyst is calculated from the broadening of diffraction lines having a maximum in the vicinity of a diffraction angle ($2\theta$) of 44° when CuK$\alpha$ beam is used as an X-ray source. The lowermost value of the average crystallite diameter may be acceptable if it is a larger value than a crystal unit. The lowermost value is actually 1 nm or more.

The average crystallite diameter of a ruthenium catalyst can be reduced to 20 nm or less if reduction is performed at a temperature of more than 180° C. and 220° C. or less within the reduction conditions of the embodiment for a reduction time within a week. Furthermore, it is preferable that the concentration of a ruthenium catalyst precursor in an aqueous solution containing a metal salt in a reductive reaction is set to be 50 mass % or less in view of suppressing an increase of the average crystallite diameter. Furthermore, a reduction treatment is more preferably performed in the presence of a dispersant in view of suppressing an increase of the average crystallite diameter.

[2] Cycloolefin Production Method

The cycloolefin production method of the embodiment includes a step of preparing a ruthenium catalyst by the aforementioned method and subjecting a monocyclic aromatic hydrocarbon to partial hydrogenation using the resultant ruthenium catalyst. More specifically, this is a method for producing a cycloolefin by subjecting a monocyclic aromatic hydrocarbon to a partial hydrogenation reaction performed in an aqueous phase (catalyst slurry) containing a ruthenium catalyst obtained by the reduction method of the embodiment and/or a ruthenium catalyst precursor and an aqueous solution containing a metal salt.

Furthermore, in repeatedly or continuously performing the partial hydrogenation reaction of a monocyclic aromatic hydrocarbon using the ruthenium catalyst, (1) a first step of bringing at least part of the ruthenium catalyst contained in the aqueous phase into contact with oxygen and (2) a second step of holding at least part of an aqueous phase containing the ruthenium catalyst obtained through the first step at a temperature within the range of more than 180° C. and 220° C. or less and at a hydrogen partial pressure within the range of 0.6 MPa or more and 5 MPa or less are included.

(1) Partial Hydrogenation Reaction (a) Raw Material

Examples of a monocyclic aromatic hydrocarbon to be used as a raw material for the partial hydrogenation reaction in the embodiment include not only benzene but also an alkyl benzene having a lower alkyl group of 1 to 4 carbon atoms such as toluene and xylene, and an alkylphenyl benzene such as phenyl benzene, which is not a condensed polycyclic aromatic hydrocarbon.

The partial hydrogenation reaction requires water and the amount of water varies depending upon reaction form. The amount of water is preferably 0.5 to 20 times by mass standard as large as the amount of monocyclic aromatic hydrocarbon as a raw material. If the amount of water falls within the range, selectivity of a cycloolefin tends to be successfully maintained without increasing the size of a reactor. The amount of water is more preferably 1 to 10 times by mass standard as large as the amount of monocyclic aromatic hydrocarbon as a raw material. In the case where the amount of water is larger or small, a sufficient amount of water is present in a reaction system to separate an organic liquid phase (hereinafter, also referred to as "oil phase") containing a raw material and a reaction product as major components, and an aqueous phase containing water as a main component, in short, to obtain a state where an oil phase is separated from an aqueous phase.

(b) Metal Salt

A metal salt must be present in the reaction system. The metal salt is preferably present in an aqueous phase in a state where at least part or whole of the metal salt is dissolved. Examples of a metal constituting the metal salt include zinc, iron, cadmium, gallium, indium, aluminium, chromium, manganese, cobalt and copper. Furthermore, examples of the metal salt include a nitrate, an acetate, a phosphate and a sulfate of a metal as mentioned above. Alternatively, a double salt containing such metal salts may be used. These metal salts may be used alone or in combination with two or more types. In view of improving cycloolefin yield, zinc sulfate is particularly preferably used as a metal salt.

Furthermore, in view of stabilizing catalyst performance, a zinc salt such as zinc hydroxide and zinc oxide is preferable. In particular, a double salt containing zinc hydroxide is preferable. As an example of the double salt, a double salt represented by the general formula $(ZnSO_4)_m \cdot (Zn(OH)_2)_n$ (m:n=1: 0.01 to 100) is preferable.

Furthermore, other than those mentioned above, the following metal salts may be present in the reaction system. Examples of a metal constituting such a metal salt include a metal of the 1st family such as lithium, sodium and potassium and a metal of the 2nd family such as magnesium and calcium according to the periodic table (the number of the families follows the IUPAC inorganic chemical nomenclature, revised version (1989)) or lead, arsenic, germanium, vanadium, silver, gold, platinum, palladium, barium and boron. Furthermore, examples of the metal salt include a nitrate, an oxide, a hydroxide, an acetate, a phosphate and a mixture of two or more salts chemically or physically blended.

The metal salt concentration of the aqueous phase in a reaction system is not particularly limited; however, it is preferably $1 \times 10^{-5}$ to 5.0 mol/L. In the case where a metal salt containing zinc sulfate is used, the concentration of a metal salt in an aqueous phase is more preferably $1 \times 10^{-3}$ to 2.0 mol/L and further preferably, 0.1 to 1.0 mol/L. Furthermore, the amount of metal salt is preferably $1 \times 10^{-5}$ to $1 \times 10^5$ times by mass standard as large as the amount of ruthenium in a ruthenium catalyst. These metal salts may present at any site within a reaction system. It is not necessary that a whole amount of metal salt is dissolved in an aqueous phase and a metal salt may be present in an oil phase. The metal salt is partly precipitated in an aqueous phase or an oil phase.

The aqueous phase is preferably acidic since the activity of a ruthenium catalyst tends to increase. In view of this point, in order to maintain an aqueous phase to be acidic, for example, an acid component such as nitric acid, sulfuric acid, acetic acid and phosphoric acid may be contained in the reaction system. In particular, sulfuric acid is preferable because it is effective to facilitate a reaction rate.

In view of obtaining a desired cycloolefin stably for a long time, the pH of the aqueous solution of a metal salt contained in the aqueous phase is preferably 7.5 or less, and more preferably 2 to 6.5. If the pH of the aqueous solution of a metal salt exceeds 7.5, the stability of a metal salt in partial hydrogenation reaction conditions reduces and a metal salt precipitates on a ruthenium catalyst, with the result that the activity of the catalyst easily reduces.

(c) Reaction Conditions

When a monocyclic aromatic hydrocarbon is partially hydrogenated with hydrogen, the hydrogen partial pressure is in general preferably 1 to 20 MPa and more preferably 2 to 7 MPa. If the hydrogen partial pressure is 1 MPa or more, selectivity of a cycloolefin tends to increase. If the hydrogen partial pressure is 20 MPa or less, necessity of increasing the pressure of hydrogen and a monocyclic aromatic hydrocarbon to be supplied to a reactor is reduced and tends to suppress inefficiency. Furthermore, the reaction temperature of a partial hydrogenation reaction is preferably 50 to 250° C. and more preferably 100 to 200° C. If the reaction temperature is 50° C. or more, a sufficient reaction rate tends to be successfully ensured. If the reaction temperature is 250° C. or less, the rapid reduction of the catalytic activity due to a growth (sintering) of the average crystallite diameter of a ruthenium catalyst during a partial hydrogenation reaction can be successfully suppressed.

The partial hydrogenation reaction of a monocyclic aromatic hydrocarbon is preferably a liquid phase reaction. The partial hydrogenation reaction can be performed by a continuous system or a batch system by use of a single reactor or two or more reactors in accordance with a liquid-phase suspension method. Furthermore, in place of the liquid-phase suspension method, a partial hydrogenation reaction can be performed also in an immobilized bed system having a ruthenium catalyst immobilized thereon. As such an immobilization method, a method of using an immobilized bed filled with a ruthenium catalyst having a sufficient size to be filled and passing a monocyclic aromatic hydrocarbon, an aqueous solution of a metal salt and hydrogen simultaneously to the immobilized bed, and a method of supplying a monocyclic aromatic hydrocarbon and hydrogen from the lower portion of an immobilized bed while holding a ruthenium catalyst and an aqueous solution of a metal salt in the immobilized bed, may be included.

In the case where the partial hydrogenation reaction is performed by the liquid-phase suspension method, to improve dissolution rates of hydrogen and a monocyclic aromatic hydrocarbon in an aqueous phase, it is preferred to perform stirring and mixing sufficiently. Furthermore, a gas introduction pipe for introducing hydrogen into catalyst slurry is preferably provided.

Next, in repeatedly or continuously performing the partial hydrogenation reaction of a monocyclic aromatic hydrocarbon using the ruthenium catalyst in the embodiment, (1) a first step of bringing at least part of the ruthenium catalyst contained in the aqueous phase into contact with oxygen and (2) a second step of holding at least part of an aqueous phase containing the ruthenium catalyst obtained through the first step at a temperature within the range of more than 180° C. and 220° C. or less and at a hydrogen partial pressure within the range of 0.6 MPa or more and 5 MPa or less will be explained.

[First Step]

The first step of the cycloolefin production method of the embodiment is a step of bringing at least part of a ruthenium catalyst contained in an aqueous phase into contact with oxygen.

In the first step, prior to bringing a ruthenium catalyst into contact with oxygen, catalyst slurry may be taken out from a reaction system (a reactor). The amount of catalyst slurry to be taken out from the reaction system may be the whole or part of catalyst slurry contained in the reactor. The amount of catalyst slurry may be appropriately selected depending upon the reaction system of partial hydrogenation reaction (batch system or continuous system). Furthermore, in the first step, a method of bringing the ruthenium catalyst contained in catalyst slurry into contact with oxygen may be a batch system or a continuous system.

In the case where a cycloolefin is produced by a batch system, the amount of catalyst slurry brought into contact with oxygen is preferably 5 to 100 mass % based on the catalyst slurry in a reactor used in the reaction, and more preferably 10 to 60 mass %. If the amount of catalyst slurry falls within the range, even if a partial hydrogenation reaction is repeatedly performed, a cycloolefin can be easily obtained stably in a high yield. Furthermore, in the case where a cycloolefin is produced by a continuous system, the amount of catalyst slurry brought into contact with oxygen is preferably controlled depending upon the reduction degree of catalyst performance per hour. For example, 5 to 80 mass % of the catalyst slurry is preferably brought into contact with oxygen within 24 hours and more preferably 10 to 60 mass % thereof is brought into contact with oxygen. If the amount of catalyst slurry brought into contact with oxygen falls within the range, cycloolefin yield tends to be particularly high.

Furthermore, prior to the first step, an oil phase involved in catalyst slurry is preferably removed. Examples of the method for removing an oil phase include settled separation and a method of blowing an inert gas such as nitrogen into catalyst slurry to distill away the oil phase involved therein. It is preferable to heat the aqueous phase to 50 to 90° C. in blowing an inert gas, because the time required for removing the oil phase can be reduced.

In the first step, as the state of catalyst slurry, a state where a ruthenium catalyst is dispersed in water like slurry is preferred since excessive oxidation of ruthenium caused by a rapid reaction between ruthenium in the catalyst with oxygen is suppressed, thereby suppressing catalyst performance reduction. The water content of the catalyst slurry may be small. However, in view of diffusing the reaction heat between ruthenium and oxygen and suppressing a rapid reaction, it is preferable that at least the surface of a ruthenium catalyst is covered with water. Particularly, since an activity recovery effect obtained by bringing a ruthenium catalyst into contact with oxygen tends to be high, the ruthenium catalyst is preferably dispersed in a neutral or acidic aqueous solution containing a metal salt used in a partial hydrogenation reaction.

Examples of an oxygen source to be brought into contact with a ruthenium catalyst include a gas containing a molecular oxygen such as an oxygen-containing gas and the air, or a compound generating a nascent state oxygen such as hydrogen peroxide. The oxygen-containing gas is preferably oxygen gas or oxygen gas diluted with an appropriate inert gas since it is simply operated.

The oxygen concentration of catalyst slurry to be brought into contact with oxygen is preferably $1 \times 10^{-7}$ to 1 N mL/mL, in terms of oxygen gas in a standard state, and more preferably $1 \times 10^{-5}$ to 0.1 N mL/mL. If the oxygen concentration falls within the range, a contact treatment is only performed relatively in a short time and ruthenium on the surface of a ruthenium catalyst tend to be successfully prevented from causing irreversible change due to abrupt oxidation. Note that the oxygen concentration of catalyst slurry can be measured by a commercially available oxygen meter.

Oxygen to be brought into contact with a ruthenium catalyst is directly supplied to the catalyst slurry. A particularly preferable method for supplying oxygen is supplying a gas containing oxygen to catalyst slurry.

This method is preferable since it is simply operated. An operation for bringing a ruthenium catalyst into contact with oxygen can be performed under any of reduced pressure, normal pressure and pressurization conditions. Accordingly, pressurization can be made in order to enhance the oxygen concentration of catalyst slurry. The temperature of an aqueous phase in bringing catalyst slurry into contact with oxygen is preferably 0 to 300° C., more preferably 30 to 200° C. and further preferably 50 to 150° C. If the temperature of an aqueous phase falls within the range, effect of regenerating a ruthenium catalyst by oxygen and an effect of preventing deterioration of a ruthenium catalyst tend to be produced in a balanced manner. Furthermore, the time for bringing a ruthenium catalyst into contact with oxygen is preferably controlled depending upon a reduction degree of catalyst performance such as activity, and is usually, several minutes to several days.

Before or after the first step, a step of holding a ruthenium catalyst under an atmosphere having substantially no hydrogen (hydrogen partial pressure is 0 MPa) and at a temperature not less than the temperature of the partial hydrogenation reaction minus 50° C. may be provided. Furthermore, the atmosphere may be a pressurized atmosphere by an inert gas such as nitrogen and argon. In this step, in view of recovering the activity of a ruthenium catalyst, an atmosphere containing hydrogen is not preferred. In this step, a ruthenium catalyst may be held in a gaseous phase where hydrogen is substantially not present or a liquid phase surrounded by the atmosphere where hydrogen is substantially not present; however, a ruthenium catalyst is preferably held in a liquid phase while stirring because the temperature of a ruthenium catalyst tends to be successfully and uniformly maintained. In this step, the ambient temperature around the catalyst is a temperature not less than the temperature of the partial hydrogenation reaction minus 50° C., preferably a temperature not less than the temperature of the partial hydrogenation reaction minus 40° C. and more preferably a temperature not less than the temperature of the partial hydrogenation reaction minus 30° C. If the ambient temperature is higher than the temperature, an active center of a catalyst sometimes irreversibly changes. Therefore, it is preferable to select the upper limit of the ambient temperature suitable for the properties of the catalyst. For example, if a micro particle catalyst containing a ruthenium metal is used as a ruthenium catalyst, it is preferable that the ambient temperature around the catalyst is not more than 250° C., more preferably not more than 200° C. and further preferably not more than 180° C. By virtue of this, it is possible to efficiently prevent physical denaturation of a ruthenium catalyst. In this step, the holding time is usually several minutes to several days. In the case where the first step is combined with this step, the order of these steps is not particularly limited.

[Second Step]

The second step of the method of producing a cycloolefin of the embodiment is a step of reducing at least part of an aqueous phase containing the ruthenium catalyst obtained through the first step by holding the aqueous phase at a temperature within the range of more than 180° C. and 220° C. or less and at a hydrogen partial pressure within the range of 0.6 MPa or more and 5 MPa or less. More specifically, in the second step, a heat treatment is performed by specifically pressurizing by hydrogen. In this respect that a catalyst is held under pressurized atmosphere by hydrogen, this step clearly differs from the step in which a ruthenium catalyst is held under an atmosphere having substantially no hydrogen (hydrogen partial pressure is 0 MPa) and at a temperature not less than the temperature of the partial hydrogenation reaction minus 50° C. that may be used as an operation for recovering the activity of the ruthenium catalyst.

In the second step, at least part of the aqueous phase (catalyst slurry) containing the ruthenium catalyst obtained through the first step is held at a temperature within the range of more than 180° C. and 220° C. or less and at a hydrogen partial pressure within the range of 0.6 MPa or more and 5 MPa or less, and more preferably at a temperature within the range of 185° C. or more and 210° C. or less and, at a hydrogen partial pressure within the range of 1 MPa or more and 4.5 MPa or less. If the holding temperature is 180° C. or less or a hydrogen partial pressure is less than 0.6 MPa, the effect of improving cycloolefin selectivity in the partial hydrogenation reaction in the second step cannot be obtained. In contrast, if the holding temperature exceeds 220° C., cycloolefin selectivity in the partial hydrogenation reaction reduces; at the same time, the average crystallite diameter of a ruthenium catalyst grows (sintering) and catalytic activity rapidly reduces. Furthermore, if the catalyst is held at a hydrogen partial pressure of more than 5 MPa, cycloolefin selectivity and activity of the catalyst easily reduce.

In the second step, examples of the gas except for hydrogen may include an inert gas such as nitrogen, helium, argon and methane. The whole pressure in the second step is determined by the sum of water vapor pressure at the treatment temperature, a hydrogen partial pressure and the partial pressure of an inert gas such as nitrogen, helium, argon and methane. When an inert gas is not present, the whole pressure in the second step is the sum of water vapor pressure and hydrogen partial pressure.

When an inert gas is not present, the hydrogen partial pressure is a value obtained by subtracting water vapor pressure at a treatment temperature from the whole pressure of the second step. To describe more specifically, a desired hydrogen partial pressure condition can be set by holding catalyst slurry to be treated at a treatment temperature and thereafter pressurizing the slurry by hydrogen so as to obtain a predetermined hydrogen partial pressure. When a gas mixture of hydrogen and an inert gas is used, pressurization may be performed depending upon the content of hydrogen, more specifically, by the gas mixture of hydrogen and an inert gas such that a value by multiplying a pressurization value of hydrogen and the inert gas by a hydrogen content is equal to a desired hydrogen partial pressure.

Furthermore, in holding catalyst slurry for a predetermined time, the catalyst slurry is preferably held while e.g., stirring so as to have a uniform concentration. Furthermore, to increase the contact area between gaseous-phase hydrogen and the catalyst slurry, for example, a baffle is preferably provided in a processing vessel. The holding time is preferably about 1 minute to 400 hours and more preferably 5 minutes to 24 hours.

When a ruthenium catalyst is in the form of e.g., particle and it is worried about pulverization by stirring, a second step can be performed by pressurizing an immobilized bed filled with the catalyst by hydrogen in an aqueous solution of a metal salt and holding the bed at a temperature within the range of more than 180° C. and 220° C. or less.

The amount of catalyst slurry to be subjected to a second step is preferably 1 to 100 mass % of the catalyst slurry obtained through the first step. The amount of catalyst slurry to be subjected to the second step is preferably controlled depending upon the cycloolefin selectivity and catalyst activity.

The cycloolefin production method of the embodiment may further contain (3) a third step in which the aqueous phase containing the ruthenium catalyst obtained through the second step is subjected to the reaction system of the partial hydrogenation reaction (refilling). The refilling method may be a method of filling a reactor with catalyst slurry obtained through the second step in the state that partial hydrogenation reaction is stopped, or a method of filling a reactor with catalyst slurry obtained through the second step in the state that a partial hydrogenation reaction proceeds.

The catalyst slurry obtained through the second step is in the state where high cycloolefin selectivity can be obtained. The state is unstable. Accordingly, when the treatment temperature and pressure of the second step differs from the reaction temperature and pressure of a partial hydrogenation reaction, it is preferable that it does not take a long time to transfer the catalyst slurry obtained through the second step to partial hydrogenation reaction conditions. A preferable change rate from the treatment temperature of the second step to the reaction temperature of a partial hydrogenation reaction is between 300° C./minute to 10° C./minute, and more preferably between 100° C./minute to 1° C./minute. The catalyst slurry obtained through the second step can be allowed to stand still for several days and then subjected to a partial hydrogenation reaction. In this case, the catalyst slurry obtained through the second step, after it is cooled to room temperature at the aforementioned change rate, is preferably held under hydrogen or under an inert gas such as nitrogen at normal pressure to 5 MPa. When treatment pressure of the second step differs from the pressure of the partial hydrogenation reaction, after the temperature of the catalyst slurry obtained through the second step reaches the reaction temperature of the partial hydrogenation reaction or at the same time the temperature is controlled, the pressure can be controlled to the pressure of the partial hydrogenation reaction.

In the case where the cycloolefin production method of the embodiment is performed by a continuous system, a mode carrying out the first, second and third steps are not particularly limited. For example, first, prior to the first step, a continuous reaction is once terminated and an oil phase is removed from a reactor. Subsequently, while the whole catalyst slurry is allowed to remain in the reactor, a ruthenium catalyst thereof is allowed to be contact with oxygen (first step). Thereafter, the catalyst slurry is held at a temperature within the range of more than 180° C. and 220° C. or less and a hydrogen partial pressure within the range of 0.6 MPa or more and 5 MPa or less for a predetermined time while stirring (second step). Thereafter, using the catalyst slurry, a partial hydrogenation reaction is started again (third step). Alternatively, first, the catalyst slurry is partly taken out without terminating a continuous reaction, and a ruthenium catalyst thereof is brought into contact with oxygen (first step). Subsequently, the catalyst slurry obtained through the first step is held at a temperature within the range of more than 180° C. and 220° C. or less and a hydrogen partial pressure within the range of 0.6 MPa or more and 5 MPa or less for a predetermined time while stirring (second step). Thereafter, the reactor is refilled with the catalyst slurry obtained through the second step and the catalyst slurry may be subjected to the reaction system of the partial hydrogenation reaction (third step).

Next, a production apparatus realizing the cycloolefin production method of the embodiment will be described.

An apparatus for producing a cycloolefin of the embodiment has
  a reactor storing an aqueous phase containing a ruthenium catalyst and an aqueous solution containing a metal salt,
  an oil/water separation vessel connected to the reactor,
  an oxygen treater connected to the oil/water separation vessel, and
  a hydrogen treater connected to the oxygen treater,
  wherein a monocyclic aromatic hydrocarbon is supplied to the reactor, at least part of an aqueous phase containing the ruthenium catalyst and at least part of the reaction solution is supplied to the oil/water separation vessel and the aqueous phase discharged from the oil/water separation vessel is introduced to the oxygen treater and brought into contact with oxygen, and thereafter introduced into the hydrogen treater.

FIG. 1 is a schematic view showing an example of a cycloolefin production apparatus of the embodiment.

A cycloolefin production apparatus 100 has a reactor 1, which has an oil/water separation vessel 10 for separating an aqueous phase containing a ruthenium catalyst and a partial hydrogenation reaction solution of a monocyclic aromatic hydrocarbon, an oxygen treater 17 connected to the oil/water separation vessel 10 by way of a pipe 9, and a hydrogen treater 26 connected to the oxygen treater 17 by way of a pipe 11.

To the reactor 1, for example, benzene as a monocyclic aromatic hydrocarbon is supplied from a benzene supply unit 15, a hydrogen gas from a hydrogen supply apparatus 14 and an acidic aqueous solution containing a metal salt from an acidic aqueous solution supply apparatus 33 through supply nozzles 14A, 15A, and 33A, respectively. The reactor 1 stores an aqueous phase containing an acidic aqueous solution containing a metal salt and a ruthenium catalyst. In the reactor, the partial hydrogenation reaction of a monocyclic aromatic hydrocarbon proceeds with hydrogen gas and benzene while controlling the temperature by a heating heater 2. The reactor 1 preferably has a stirrer 3 for stirring the interior thereof.

The reactor 1 has the oil/water separation vessel 10 attached therein for separating the reaction solution, that is, an oil phase, containing a reaction product produced by a partial hydrogenation reaction and an unreacted monocyclic aromatic hydrocarbon as major components, from an aqueous phase containing a ruthenium catalyst. The reactor 1 and the oil/water separation vessel 10 are partly divided by a partition wall 34. Owing to the wall, the oil/water separation vessel 10 is rarely affected by stirring by the stirrer 3. Furthermore, through the portion at which no partition wall 34 is provided, an oil phase and an aqueous phase move while keeping a mixture state from the reactor 1 to the oil/water separation vessel 10. The oil/water separation vessel 10 preferably has a sufficient volume for separating an aqueous phase and an oil phase within a predetermined time. As described above, the reaction solution of a partial hydrogenation reaction is an oil phase containing a raw material, that is, a monocyclic aromatic hydrocarbon such as benzene and a reaction product, that is, cycloolefin, as major components. The oil phase is separated from an aqueous phase containing a ruthenium catalyst in the oil/water separation vessel 10. Note that in this example, the oil/water separation vessel 10 is attached within the reactor 1; however, the oil/water separation vessel 10 may be attached outside the reactor 1 and connected to the reactor 1 by way of a pipe.

The oil phase separated in the oil/water separation vessel 10 is supplied from an overflow nozzle to a separator 6 by way of a pipe 8 and cooled in the separator 6 to separate water dissolved in the oil phase. The water separated is supplied by means of a pump 5 to the reactor 1. The oil phase from which water is separated is transferred to a cycloolefin separation step by way of a pipe 7.

The aqueous phase separated by the oil/water separation vessel 10 flows by way of a pipe 9 and is regulated in flow rate by a pressure drop valve 22 and supplied to the oxygen treater 17 by way of a pipe 19. In the oxygen treater 17, an aqueous phase containing a ruthenium catalyst is brought into contact with oxygen to allow at least part of the ruthenium catalyst to contact with oxygen. The oxygen treater 17 preferably has a stirrer 23 for stirring the aqueous phase containing the ruthenium catalyst supplied thereto. Furthermore, the oxygen treater 17 is preferably covered with a heating jacket 17A so as to easily control the interior temperature thereof. Furthermore, the production apparatus 100 preferably has a gas supply apparatus 21 and a gas introduction nozzle 21A connecting the gas supply apparatus 21 and the oxygen treater 17 so as to introduce a gas containing a predetermined concentration of oxygen. By virtue of this, it is preferable to directly introduce a gas into an aqueous phase containing a ruthenium catalyst. Furthermore, to the oxygen treater 17, a condenser 25 may be connected. Of the gas containing e.g., oxygen and vaporized aqueous phase, the aqueous phase is condensed by the condenser 25 and returned again to the oxygen treater 17, whereas the gas containing e.g., oxygen is discharged outside by way of a pipe 24.

An aqueous phase containing a ruthenium catalyst and brought into contact with oxygen in the oxygen treater 17 is fed by way of a pipe 11, regulated in flow rate by a pump 12 and supplied to a hydrogen treater 26 by way of a pipe 13. In the hydrogen treater 26, an aqueous phase containing a ruthenium catalyst is introduced thereto and held at a temperature within the range of more than 180° C. and 220° C. or less and a hydrogen partial pressure within the range of 0.6 MPa or more and 5 MPa or less for a predetermined time. The hydrogen treater 26 has heat resistance tolerable to 220° C. or more and pressure resistance tolerable to 8 MPa or more. The hydrogen treater 26 preferably has a stirrer 27 for stirring an aqueous phase containing a ruthenium catalyst to be supplied thereto. Furthermore, the hydrogen treater 26 is preferably covered with a heating heater 32 to easily control the interior temperature thereof. Furthermore, the production apparatus 100 has a hydrogen supply apparatus 30 and a supply nozzle 30A connected between the hydrogen supply apparatus 30 and the hydrogen treater 26 so as to introduce hydrogen. By virtue of this, it is preferable to directly introduce a gas into an aqueous phase containing a ruthenium catalyst.

As an example of the hydrogen treater 26, other than a treater of a stirring/mixing vessel type shown in the figure, a static mixer type treater equipped with a heating heater is included.

The aqueous phase containing a ruthenium catalyst treated under hydrogen in the hydrogen treater 26 is supplied to the reactor 1 by way of a pipe 28, a pump 29 and a pipe 31.

In the cycloolefin production apparatus 100, the reactor 1, the oil/water separation vessel 10, the oxygen treater 17, the hydrogen treater 26 and the pipes connecting the apparatuses are each formed of a metal material such as carbon steel and stainless steel. In each of the apparatuses, at least a portion in contact with the reaction solution is preferably formed of a nickel-containing material. For example, the inner wall (inner surface) of the reactor 1 is preferably formed of a material capable of reducing a metal elution rate such as a molybdenum-containing nickel based alloy or a molybdenum and chromium-containing nickel based alloy.

Examples of the molybdenum-containing nickel based alloy used herein include, but not particularly limited to, Hastelloy A, Hastelloy B, Hastelloy B-3 and Hastelloy B-2 (these are trade names, which are heat resistant nickel alloys produced by Hayues stellite Co.). Similarly, examples of the molybdenum and chromium-containing nickel based alloy include, but not particularly limited to, Hastelloy C, Hastelloy C-276, Hastelloy C-4, Hastelloy C-22, Hastelloy C-2000, Hastelloy G, Hastelloy G-2, Hastelloy G-3, Hastelloy G-30, Hastelloy H and Hastelloy W (these are trade names, which are heat resistant nickel alloys produced by Hayues stellite Co.), incolloy 825 (trade name, produced by Inco Alloys International, Inc.) and MAT21 (trade name, produced by Mitsubishi Materials Corporation).

Figure 2:
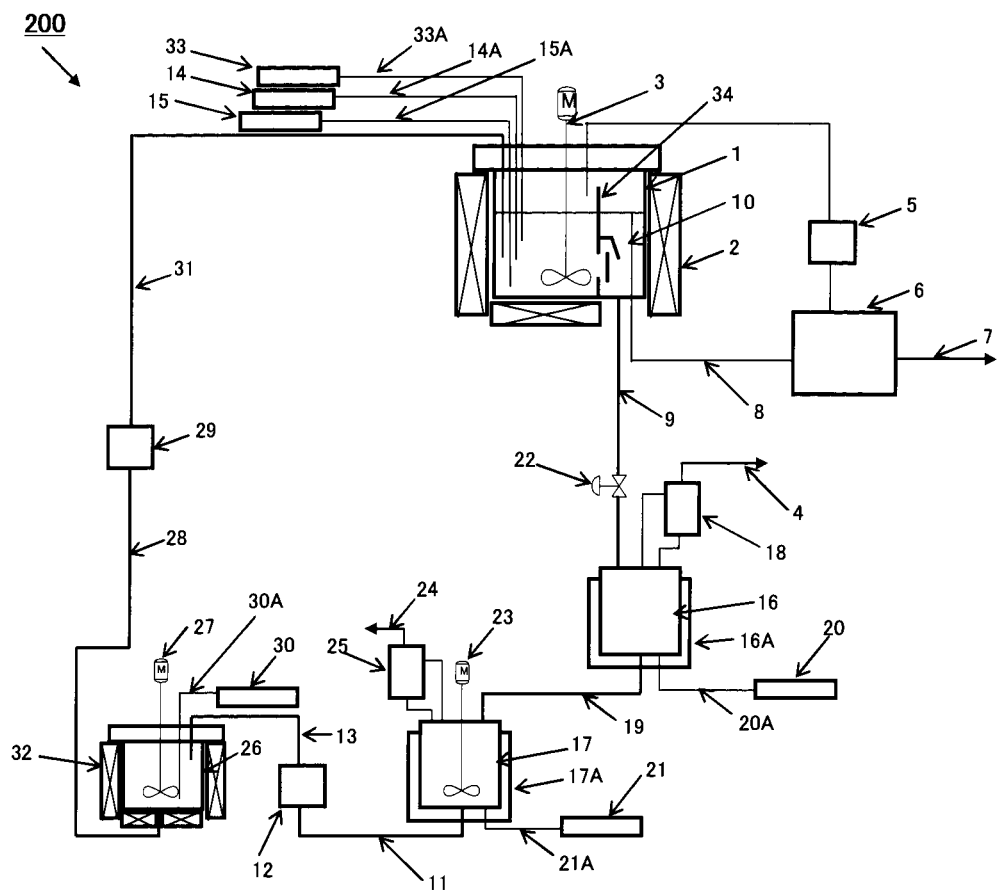
FIG. 2 is a schematic view showing another embodiment of a cycloolefin production apparatus of the present invention.

FIG. 2 is a schematic view showing another example of a cycloolefin production apparatus of the embodiment.

A cycloolefin production apparatus 200 further has an oil stripping vessel 16 between the oil/water separation vessel 10 and the oxygen treater 17 connecting them. The production apparatus 200 has the like members as those of the production apparatus 100 as shown in FIG. 1 and further explanation is omitted for brevity's sake. Note that in the oxygen treater 17, to which an aqueous phase is supplied through the oil/water separation vessel 10 and the oil stripping vessel 16 sequentially in this order, at least part of the ruthenium catalyst contained in the aqueous phase is brought into contact with oxygen.

In the aqueous phase separated by the oil/water separation vessel 10, a small amount of oil phase is sometimes inevitably contained. Thus, the aqueous phase preferably passes through the pipe 9 while being regulated in flow rate by the pressure drop valve 22 and is supplied to the oil stripping vessel 16. The oil stripping vessel 16 is used for removing an oil phase, which is dissolved or dispersed in an aqueous phase containing a ruthenium catalyst, from the aqueous phase. In the oil stripping vessel 16, an inert gas to a monocyclic aromatic hydrocarbon and a cycloolefin contained in the oil phase, such as nitrogen and water vapor, is blown into an aqueous phase from a gas supply apparatus 20 through a gas introduction nozzle 20A. By blowing the inert gas, an oil phase containing a monocyclic aromatic hydrocarbon and its partial hydrogenated reaction product (cycloolefin) dissolved or dispersed in the aqueous phase as major components can be removed from the aqueous phase.

The oil stripping vessel 16 is preferably covered with a heating jacket 16A so as to easily control the interior temperature thereof. Furthermore, to the oil stripping vessel 16, a condenser 18 may be connected. Of an inert gas, vaporized oil phase and the aqueous phase involved in the oil phase, the aqueous phase is condensed by the condenser 18, and returned again to the oil stripping vessel 16; at the same time, the inert gas and vaporized oil phase flow out through the pipe 4 to the outside. The aqueous phase from which the oil phase is removed by the oil stripping vessel 16 passes through the pipe 19 and is supplied to the oxygen treater 17.

Furthermore, as not shown in the figure, the production apparatus 100 or the production apparatus 200 may have a low hydrogen partial pressure treater for connecting the oxygen treater 17 and the hydrogen treater 26 between them. The low hydrogen partial pressure treater holds an aqueous phase containing a ruthenium catalyst supplied from the oxygen treater 17 under an atmosphere substantially containing no hydrogen (hydrogen partial pressure is 0 MPa) at a temperature not less than the temperature of the partial hydrogenation reaction minus 50° C., and thereby holds the ruthenium catalyst contained in the aqueous phase at the above temperature. By this operation, a ruthenium catalyst can be regenerated. The aqueous phase held by a low hydrogen partial pressure treater is supplied to the hydrogen treater 26.

EXAMPLES

The embodiments will be more specifically described by way of Examples and Comparative Examples. The embodiments will not be limited to the Examples so far as they do not depart from the spirit of the invention.

The conversion rate of benzene and the selectivity of cyclohexene shown in the following Examples were calculated in accordance with the following equations based on concentration values of benzene, cyclohexene and cyclohexane obtained by gas chromatographic analysis of the oil phase obtained.

$$\text{Conversion rate of benzene (\%)} = \frac{\text{The molar number of benzene consumed in the reaction}}{\text{The molar number of benzene supplied to the reactor}} \times 100 \quad \text{[Expression 1]}$$

$$\text{Selectively of cyclohexene (\%)} = \frac{\text{The molar number of cyclohexene produced by the reaction}}{\text{The molar number of cyclohexene produced by the reaction} + \text{the molar number of cyclohexane produced by the reaction}} \times 100 \quad \text{[Expression 2]}$$

Examples 1 to 6

Comparative Examples 1 to 4

Ruthenium chloride (RuCl$_3$.3H$_2$O) (5 g) and zinc chloride (2.0 g) were dissolved in water (500 mL) while stirring. A 30% aqueous sodium hydroxide solution (70 mL) was added at a time to the above aqueous solution while stirring. The resultant mixture was further stirred at 80° C. for 2 hours. After cooling, the mixture was allowed to stand still and the supernatant was removed by decantation. Thereafter, a black precipitate was washed five times with a 1 N aqueous sodium hydroxide solution and further washed three times with water. In the operation above, a black precipitate formed of Ru(OH)$_3$ containing Zn(OH)$_2$ was obtained. Water was added to the black precipitate obtained to bring the mixture to a total volume of 500 mL. ZrO$_2$ powder (produced by Daiichi Kigenso Kagaku Kogyo Co., Ltd., average particle size: 0.35 μm) (11.5 g) was added to the mixture, and further stirred for 1 hour at room temperature and then filtrated. In the operation mentioned above, a ruthenium catalyst precursor containing ZrO$_2$ as a dispersant was obtained. The whole amount of ruthenium catalyst precursor containing ZrO$_2$ was added to a 10 mass % aqueous solution (280 mL) of zinc sulfate (ZnSO$_4$) and a reduction treatment was performed at a reduction temperature of 200° C. under hydrogen at various pressures shown in Table 1.

Using ruthenium catalyst slurry obtained by a reduction treatment as it was, a partial hydrogenation reaction was performed at 140° C., under hydrogen at a total pressure of 5 MPa by use of benzene (140 mL) as a raw material. The cyclohexene selectivity values at a benzene conversion rate of 50% are shown in Table 1 together with reduction conditions of a ruthenium catalyst precursor.

Furthermore, with respect to a ruthenium catalyst containing ZrO$_2$ as a dispersant obtained in the reduction conditions of Example 3 and a ruthenium catalyst containing ZrO$_2$ as a dispersant obtained in the reduction conditions of Comparative Example 3 were subjected to fluorescent X-ray analysis to obtain Zn concentration. The Zn concentrations were almost the same, that is, 1.25 mass % and 1.23 mass %, respectively.

TABLE 1

| | Reduction condition for Ru catalyst precursor | | | | Ru catalyst Average crystallite diameter (nm) | Benzene partial hydrogenation reaction Cyclohexene selectivity at a benzene conversion rate of 50% (%) |
|---|---|---|---|---|---|---|
| | Temperature (° C.) | Hydrogen partial pressure (MPa) | Total pressure (MPa) | Time (hr) | | |
| Example 1 | 200 | 0.60 | 2.15 | 4.0 | 69 | 89.0 |
| Example 2 | 200 | 0.80 | 2.35 | 4.0 | 68 | 90.1 |
| Example 3 | 200 | 1.00 | 2.55 | 4.0 | 68 | 90.8 |
| Example 4 | 200 | 1.45 | 3.00 | 4.0 | 67 | 91.6 |
| Example 5 | 200 | 3.45 | 5.00 | 2.0 | 63 | 91.2 |
| Example 6 | 200 | 5.00 | 6.55 | 2.0 | 63 | 89.0 |
| Comparative Example 1 | 200 | 0.00 | 1.55 | 4.0 | 70 | 79.0 |
| Comparative Example 2 | 200 | 0.30 | 1.85 | 4.0 | 69 | 83.1 |
| Comparative Example 3 | 200 | 0.50 | 2.05 | 4.0 | 69 | 83.9 |
| Comparative Example 4 | 200 | 5.95 | 7.50 | 2.0 | 63 | 80.3 |

Examples 7, 8 and Comparative Examples 5 to 7

A reduction treatment was performed at different reduction temperatures and pressures. The resultant ruthenium catalyst slurry samples were directly subjected to a partial hydrogenation reaction of benzene performed at 140° C. under hydrogen at a total pressure of 5 MPa. The cyclohexene selectivity values at a benzene conversion rate of 50% are shown in Table 2 together with reduction conditions of a ruthenium catalyst precursor.

TABLE 2

| | Reduction condition for Ru catalyst precursor | | | | Ru catalyst Average crystallite diameter (nm) | Benzene partial hydrogenation reaction Cyclohexene selectivity at a benzene conversion rate of 50% (%) |
|---|---|---|---|---|---|---|
| Example | Temperature (° C.) | Hydrogen partial pressure (MPa) | Total pressure (MPa) | Time (hr) | | |
| Example 7 | 185 | 1.88 | 3.00 | 4.0 | 65 | 89.1 |
| Example 8 | 220 | 0.69 | 3.00 | 4.0 | 71 | 88.4 |
| Comparative Example 5 | 150 | 2.52 | 3.00 | 6.0 | 55 | 82.5 |
| Comparative Example 6 | 150 | 4.52 | 5.00 | 22 | 55 | 83.4 |
| Comparative Example 7 | 175 | 2.11 | 3.00 | 4.0 | 61 | 83.4 |
| Comparative Example 8 | 230 | 2.21 | 5.00 | 4.0 | 75 | 60.3 |

Example 9

A reduction treatment was performed under the conditions shown in Comparative Example 6. The resultant ruthenium catalyst slurry was directly subjected to a reduction treatment performed under the conditions shown in Table 3 and thereafter subjected to a partial hydrogenation reaction of benzene performed at 140° C. under hydrogen at a total pressure of 5 MPa. The cyclohexene selectivity at a benzene conversion rate of 50% is shown in Table 3 together with reduction conditions of ruthenium catalyst.

TABLE 3

| Example | Reduction condition for Ru catalyst precursor | | | | Ru catalyst Average crystallite diameter (nm) | Benzene partial hydrogenation reaction Cyclohexene selectivity at a benzene conversion rate of 50% (%) |
|---|---|---|---|---|---|---|
| | Temperature (° C.) | Hydrogen partial pressure (MPa) | Total pressure (MPa) | Time (hr) | | |
| Example 9 | 200 | 1.45 | 3.00 | 4 | 67 | 91.7 |

Example 10

Preparation of Ruthenium Catalyst Slurry of an Aqueous Cobalt Sulfate Solution Containing Zirconia as a Dispersant Ruthenium chloride ($RuCl_3 \cdot 3H_2O$) (5 g) and zinc chloride (13.0 g) were dissolved in water (500 mL) while stirring. A 30% aqueous sodium hydroxide solution (70 mL) was added at a time to the above aqueous solution while stirring. The resultant mixture was further stirred at 80° C. for 2 hours. After cooling, the mixture was allowed to stand still and the supernatant was removed by decantation. Thereafter, a black precipitate was washed three times with a 1 N aqueous sodium hydroxide solution. In the operation above, a black precipitate formed of $Ru(OH)_3$ containing $Zn(OH)_2$ was obtained. To the black precipitate, a 5% aqueous sodium hydroxide solution was added to bring the mixture to a total volume of 500 mL. Reduction was performed under hydrogen pressurization at 150° C., 5 MPa for 10 hours. The reaction solution was cooled and the resultant black precipitate was filtrated under an argon atmosphere, and washed first with a 30% aqueous sodium hydroxide solution and then with water. Thereafter, the precipitate was dried under vacuum to obtain 2.3 g of a ruthenium catalyst precursor. The ruthenium catalyst precursor had an average crystallite diameter of 5.1 nm and contained zinc in an amount of 7.2 mass %. The resultant ruthenium catalyst precursor (1.0 g) and a zirconia ($ZrO_2$) powder (produced by Daiichi Kigenso Kagaku Kogyo Co., Ltd., average particle size 0.35 μm) (5.0 g) were added to a 10 mass % aqueous cobalt sulfate solution (280 mL) to prepare catalyst precursor slurry. The catalyst precursor slurry was stirred under hydrogen and in the conditions of 200° C. and a total pressure of 5 MPa (hydrogen partial pressure 3.5 MPa) for 2 hours to prepare a ruthenium catalyst slurry containing zirconia as a dispersant in an aqueous cobalt sulfate solution.

(Partial Hydrogenation Reaction of Benzene Using a Ruthenium Catalyst in an Aqueous Cobalt Sulfate Solution)

The ruthenium catalyst slurry obtained above was directly cooled to a temperature of 140° C. for 15 minutes and benzene (140 mL) was added at a total pressure of 5 MPa to perform a benzene partial hydrogenation reaction. As a result, the cyclohexene selectivity at a benzene conversion rate of 50% was 82.7%.

(Oxygen Treatment and Hydrogen Treatment of Ruthenium Catalyst Slurry)

After the above catalyst slurry subjected to the benzene partial hydrogenation reaction was cooled to room temperature, an oil phase was separated and removed by bubbling nitrogen into the catalyst slurry while stirring at 80° C. and bubbling of nitrogen containing 3% oxygen was performed at 80° C. for 5 hours. The catalyst slurry (240 mL) obtained was stirred under hydrogen and in the conditions of 200° C. and a total pressure of 5 MPa (hydrogen partial pressure 3.5 MPa) for 2 hours.

(Benzene Partial Hydrogenation Reaction of Catalyst Slurry Treated with Oxygen and Hydrogen)

The catalyst slurry (240 mL) treated as described above was cooled to a temperature of 140° C. for 15 minutes and benzene (120 mL) was added at a total pressure of 5 MPa and a benzene partial hydrogenation reaction was performed at 140° C. As a result, the cyclohexene selectivity at a benzene conversion rate of 50% was 83.4%.

Comparative Example 9

In the same manner as in Example 10, catalyst precursor slurry composed of a ruthenium catalyst precursor (1.0 g), zirconia ($ZrO_2$) powder (produced by Daiichi Kigenso Kagaku Kogyo Co., Ltd., average particle size 0.35 μm) (5.0 g) and a 10 mass % aqueous cobalt sulfate solution (280 mL) was prepared. To the ruthenium catalyst precursor slurry, benzene (140 mL) was added at 140° C. and a total pressure of 5 MPa to perform a benzene partial hydrogenation reaction. As a result, the cyclohexene selectivity at a benzene conversion rate of 50% was 75.3%.

The catalyst precursor slurry subjected to the benzene partial hydrogenation reaction was treated with oxygen in the same manner as in Example 10 and then stirred under hydrogen and in the conditions of 170° C. and a total pressure of 4.3 MPa (hydrogen partial pressure 3.5 MPa) for 2 hours to obtain catalyst slurry (240 mL). To the slurry, benzene (120 mL) was added in the same reaction conditions as in Example 1 to perform a benzene partial hydrogenation reaction. As a result, the cyclohexene selectivity at a benzene conversion rate of 50% was 75.6%. The results are collectively shown in Table 4.

TABLE 4

| | Second step Treatment under hydrogen pressurization | | | | Benzene partial hydrogenation reaction Cyclohexene selectivity at a benzene conversion rate of 50% (%) |
|---|---|---|---|---|---|
| | Temperature (° C.) | Hydrogen partial pressure (MPa) | Total pressure (MPa) | Time (hr) | |
| Example 10 | 200 | 3.50 | 5.05 | 2.0 | 83.4 |
| Comparative Example 9 | 170 | 3.50 | 4.29 | 2.0 | 75.6 |

Example 11

Preparation of Ruthenium Catalyst Slurry of an Aqueous Potassium Sulfate Solution Containing Zirconia as a Dispersant Ruthenium chloride ($RuCl_3 \cdot 3H_2O$) (5 g) and zinc chloride (13.0 g) were dissolved in water (500 mL) while stirring. A 30% aqueous sodium hydroxide solution (70 mL) was added at a time to the above aqueous solution while stirring. The resultant mixture was further stirred at 80° C. for 2 hours. After cooling, the mixture was allowed to stand still and the supernatant was removed by decantation. Thereafter, a black precipitate was washed three times with a 1 N aqueous sodium hydroxide solution. In the operation above, a black precipitate formed of $Ru(OH)_3$ containing $Zn(OH)_2$ was obtained. To the black precipitate obtained, a 5% aqueous sodium hydroxide solution was added to bring the mixture to a total volume of 500 mL. Reduction was performed under hydrogen pressurization at 150° C. and 5 MPa for 12 hours. The reaction solution was cooled and the resultant black precipitate was filtrated under an argon atmosphere and washed first with a 30% aqueous sodium hydroxide solution and then with water. Thereafter, the precipitate was dried under vacuum to obtain 2.3 g of a ruthenium catalyst precursor. The ruthenium catalyst precursor had an average crystallite diameter of 5.5 nm and contained zinc in an amount of 7.2 mass %. The resultant ruthenium catalyst precursor (1.0 g) and a zirconia ($ZrO_2$) powder (produced by Daiichi Kigenso Kagaku Kogyo Co., Ltd., average particle size 0.35 µm) (5.0 g) were added to a 15 mass % aqueous potassium sulfate solution (280 mL) to prepare catalyst precursor slurry. The catalyst precursor slurry was stirred under hydrogen and in the conditions of 200° C. and a total pressure of 5 MPa (hydrogen partial pressure 3.5 MPa) for 2 hours to prepare a ruthenium catalyst slurry containing zirconia as a dispersant in an aqueous potassium sulfate solution.
(Partial Hydrogenation Reaction of Benzene Using a Ruthenium Catalyst in an Aqueous Potassium Sulfate Solution)

The ruthenium catalyst slurry obtained above was directly cooled to a temperature of 140° C. for 15 minutes and benzene (140 mL) was added at a total pressure of 5 MPa to perform a benzene partial hydrogenation reaction. As a result, the cyclohexene selectivity at a benzene conversion rate of 50% was 79.7%.
(Oxygen Treatment and Hydrogen Treatment of Ruthenium Catalyst Slurry)

After the above catalyst slurry subjected to the benzene partial hydrogenation reaction was cooled to room temperature, an oil phase was separated and removed by bubbling nitrogen into the catalyst slurry while stirring at 80° C. and bubbling of nitrogen containing 3% oxygen was performed at 80° C. for 5 hours. The catalyst slurry (240 mL) obtained was stirred under hydrogen and in the conditions of 200° C. and a total pressure of 5 MPa (hydrogen partial pressure 3.5 MPa) for 2 hours.
(Benzene Partial Hydrogenation Reaction of Catalyst Slurry Treated with Oxygen and Hydrogen)

The catalyst slurry (240 mL) treated as described above was cooled to a temperature of 140° C. for 15 minutes and benzene (120 mL) was added at a total pressure of 5 MPa and a benzene partial hydrogenation reaction was performed at 140° C. As a result, the cyclohexene selectivity at a benzene conversion rate of 50% was, 80.5%.

Comparative Example 10

In the same manner as in Example 11, catalyst precursor slurry composed of a ruthenium catalyst precursor (1.0 g), zirconia ($ZrO_2$) powder (produced by Daiichi Kigenso Kagaku Kogyo Co., Ltd., average particle size 0.35 w) (5.0 g) and a 10 mass % aqueous potassium sulfate solution (280 mL) was prepared. To the ruthenium catalyst precursor slurry, benzene (140 mL) was added at 140° C. and a total pressure of 5 MPa to perform a benzene partial hydrogenation reaction. As a result, the cyclohexene selectivity at a benzene conversion rate of 50% was 65.8%.

The catalyst precursor slurry subjected to the benzene partial hydrogenation reaction was treated with oxygen in the same manner as in Example 11 and stirred under hydrogen and in the conditions of 170° C. and a total pressure of 4.3 MPa (hydrogen partial pressure 3.5 MPa) for 2 hours to obtain catalyst slurry (240 mL). To the slurry, benzene (120 mL) was added in the same reaction conditions as in Example 11 to perform a benzene partial hydrogenation reaction. As a result, the cyclohexene selectivity at a benzene conversion rate of 50% was 66.0%. The results are collectively shown in Table 5.

TABLE 5

| | Second step Treatment under hydrogen pressurization | | | | Benzene partial hydrogenation reaction Cyclohexene selectivity at a benzene conversion rate of 50% (%) |
|---|---|---|---|---|---|
| | Temperature (° C.) | Hydrogen partial pressure (MPa) | Total pressure (MPa) | Time (hr) | |
| Example 11 | 200 | 3.50 | 5.05 | 2.0 | 80.5 |
| Comparative Example 10 | 170 | 3.50 | 4.29 | 2.0 | 66.0 |

Examples 12 to 14

Preparation of Ruthenium Catalyst Slurry Containing Chromia as a Dispersant

Ruthenium chloride ($RuCl_3 \cdot 3H_2O$) (5 g) and zinc chloride (18.0 g) were dissolved in water (500 mL) while stirring. A 30% aqueous sodium hydroxide solution (70 mL) was added at a time to the above aqueous solution while stirring. The resultant mixture was further stirred at 80° C. for 2 hours. After cooling, the mixture was allowed to stand still and the supernatant was removed by decantation. Thereafter, a black precipitate was washed three times with a 1 N aqueous sodium hydroxide solution. In the operation above, a black precipitate formed of $Ru(OH)_3$ containing $Zn(OH)_2$ was obtained. To the black precipitate obtained, a 5% aqueous sodium hydroxide solution was added to bring the mixture to a total volume of 500 mL. Reduction was performed under hydrogen pressurization at 150° C. and 5 MPa for 10 hours. After the reaction solution was cooled, the resultant black precipitate was filtrated under an argon atmosphere and washed first with a 30% aqueous sodium hydroxide solution and then with water. Thereafter, the precipitate was dried under vacuum to obtain 2.4 g of a ruthenium catalyst precursor. The ruthenium catalyst precursor had an average crystallite diameter of 5.0 nm and contained zinc in an amount of 7.8 mass %. The resultant ruthenium catalyst precursor (1.0 g) and a chromia ($Cr_2O_3$) powder (produced by Wako Pure Chemical Industries, Ltd., average particle size 2.1 µm)(5.0 g) were added to a 10 mass % aqueous zinc sulfate solution (280 mL) to prepare catalyst precursor slurry. The catalyst precursor slurry was stirred under hydrogen and in the conditions of 200° C. and a total pressure of 5 MPa (hydrogen partial pressure 3.5 MPa) for 2 hours to prepare a ruthenium catalyst slurry containing chromia as a dispersant in an aqueous zinc sulfate solution.
(Partial Hydrogenation Reaction of Benzene Using a Ruthenium Catalyst in an Aqueous Zinc Sulfate Solution)

The ruthenium catalyst slurry obtained above was directly cooled to a temperature of 140° C. for 15 minutes and benzene (140 mL) was added at a total pressure of 5 MPa to perform a benzene partial hydrogenation reaction. As a result, the cyclohexene selectivity at a benzene conversion rate of 50% was 85.1%.

(Oxygen Treatment and Hydrogen Treatment of Ruthenium Catalyst Slurry)

After the catalyst slurry subjected to the benzene partial hydrogenation reaction was cooled to room temperature, an oil phase was separated and removed by bubbling nitrogen into the catalyst slurry while stirring at 80° C. and bubbling of nitrogen containing 3% oxygen was performed at 80° C. for 5 hours. The catalyst slurry obtained (240 mL) was subjected to a hydrogen treatment under hydrogen in the conditions of various temperatures and pressures shown in Table 6.

(Benzene Partial Hydrogenation Reaction of Catalyst Slurry Treated with Oxygen and Hydrogen)

The catalyst slurry (240 mL) treated as described above was cooled to a temperature of 140° C. for 15 minutes and benzene (120 mL) was added at a total pressure of 5 MPa and a benzene partial hydrogenation reaction was performed at 140° C. The cyclohexene selectivity at a benzene conversion rate of 50% is shown in Table 6 together with others.

Comparative Examples 11 and 12

In the same manner as in Examples 12 to 14, a catalyst precursor slurry composed of a ruthenium catalyst precursor (1.0 g), chromia ($Cr_2O_3$) powder (produced by Wako Pure Chemical Industries, Ltd., average particle size 2.1 μm) (5.0 g) and a 10 mass % aqueous zinc sulfate solution (280 mL) was prepared. To the ruthenium catalyst precursor slurry, benzene (140 mL) was added at 140° C. and a total pressure of 5 MPa to perform a benzene partial hydrogenation reaction. As a result, the cyclohexene selectivity at a benzene conversion rate of 50% was 77.4%.

After the benzene partial hydrogenation reaction was performed, oil phase was removed from the catalyst precursor slurry in the same manner as in Examples 12 to 14 and an oxygen treatment was performed. The resultant catalyst slurry (240 mL) was subjected to a hydrogen treatment under hydrogen in the conditions of various temperatures and pressures shown in Table 6, and thereafter benzene (120 mL) was added in the same reaction conditions as in Examples 12 to 14 to perform a benzene partial hydrogenation reaction. The cyclohexene selectivity of a benzene conversion rate of 50% is shown in Table 6 together with others.

TABLE 6

| | Second step Treatment under hydrogen pressurization | | | Benzene partial hydrogenation reaction |
|---|---|---|---|---|
| | | | | Cyclohexene selectivity at a benzene conversion rate of 50% (%) |
| | Temperature (° C.) | Hydrogen partial pressure (MPa) | Total pressure (MPa) | Time (hr) | |
| Example 12 | 200 | 3.50 | 5.05 | 2.0 | 85.6 |
| Example 13 | 185 | 3.38 | 4.50 | 2.0 | 84.1 |
| Example 14 | 220 | 3.50 | 5.81 | 2.0 | 84.2 |
| Comparative Example 11 | 170 | 3.50 | 4.29 | 2.0 | 77.6 |
| Comparative Example 12 | 230 | 3.50 | 6.29 | 2.0 | 70.3 |

Example 15

Preparation of Ruthenium Catalyst Slurry Containing Zirconia as a Dispersant

Ruthenium chloride ($RuCl_3 \cdot 3H_2O$) (5 g) and zinc chloride (15.0 g) were dissolved in water (500 mL) while stirring. A 30% aqueous sodium hydroxide solution (70 mL) was added at a time to the above aqueous solution while stirring. The resultant mixture was further stirred at 80° C. for 2 hours. After cooling, the mixture was allowed to stand still and the supernatant was removed by decantation. Thereafter, a black precipitate was washed three times with a 1 N aqueous sodium hydroxide solution. In the operation above, a black precipitate formed of $Ru(OH)_3$ containing $Zn(OH)_2$ was obtained. To the black precipitate obtained, a 5% aqueous sodium hydroxide solution was added to bring the mixture to a total volume of 500 mL. Reduction was performed under hydrogen pressurization at 150° C. and 5 MPa for 12 hours. The reaction solution was cooled and the resultant black precipitate was filtrated under an argon atmosphere and washed first with a 30% aqueous sodium hydroxide solution and then with water. Thereafter, the precipitate was dried under vacuum to obtain 2.3 g of a ruthenium catalyst precursor. The ruthenium catalyst precursor had an average crystallite diameter of 5.3 nm and contained zinc in an amount of 7.6 mass %. The resultant ruthenium catalyst precursor (1.0 g) and a zirconia ($ZrO_2$) powder (produced by Daiichi Kigenso Kagaku Kogyo Co., Ltd., average particle size 0.35 μm) (5.0 g) were added to a 10 mass % aqueous zinc sulfate solution (280 mL) to prepare catalyst precursor slurry. The catalyst precursor slurry was stirred under hydrogen and in the conditions of 200° C. and a total pressure of 5 MPa (hydrogen partial pressure 3.5 MPa) for 2 hours to prepare a ruthenium catalyst slurry containing zirconia as a dispersant in an aqueous zinc sulfate solution.

(Partial Hydrogenation Reaction of Benzene Using a Ruthenium Catalyst in an Aqueous Zinc Sulfate Solution)

The ruthenium catalyst slurry obtained above was directly cooled to a temperature of 140° C. for 10 minutes and benzene (140 mL) was added at a total pressure of 5 MPa to perform a benzene partial hydrogenation reaction. As a result, the cyclohexene selectivity at a benzene conversion rate of 50% was 87.5%.

(Oxygen Treatment and Hydrogen Treatment of Ruthenium Catalyst Slurry)

After the above catalyst slurry subjected to the benzene partial hydrogenation reaction was cooled to room temperature, an oil phase was separated and completely removed by bubbling nitrogen into the catalyst slurry while stirring at 80° C. and bubbling of nitrogen containing 3% oxygen was performed at 80° C. for 5 hours. The resultant catalyst slurry (240 mL) was stirred under hydrogen and in the conditions of 200° C. and a total pressure of 5 MPa (hydrogen partial pressure 3.5 MPa) for 2 hours.

(Benzene Partial Hydrogenation Reaction Using Catalyst Slurry Treated with Oxygen and Hydrogen)

The catalyst slurry (240 mL) treated as described above was cooled to a temperature of 140° C. for 10 minutes and benzene (120 mL) was added at a total pressure of 5 MPa and a benzene partial hydrogenation reaction at 140° C. was performed. The cyclohexene selectivity at a benzene conversion rate of 50% was 87.6%.

Comparative Example 13

In the same manner as in Example 15, catalyst precursor slurry composed of a ruthenium catalyst precursor (1.0 g), zirconia (ZrO$_2$) powder (produced by Daiichi Kigenso Kagaku Kogyo Co., Ltd., average particle size 0.35 μm) (5.0 g) and a 10 mass % aqueous zinc sulfate solution (280 mL) was prepared. To the ruthenium catalyst precursor slurry, benzene (140 mL) was added at 140° C. and a total pressure of 5 MPa to perform a benzene partial hydrogenation reaction. As a result, the cyclohexene selectivity at a benzene conversion rate of 50% was 81.3%.

From the catalyst precursor slurry subjected to the benzene partial hydrogenation reaction, an oil phase was completely removed in the same manner as in Example 15 and treated with oxygen.

The resultant catalyst slurry (240 mL) was stirred under hydrogen and in the conditions of 170° C. and a total pressure of 4.3 MPa (hydrogen partial pressure 3.5 MPa) for 2 hours, and thereafter benzene (120 mL) was added in the same reaction conditions as in Example 15 to perform a benzene partial hydrogenation reaction. As a result, the cyclohexene selectivity at a benzene conversion rate of 50% was 81.5%. The results are collectively shown in Table 7.

TABLE 7

| | Second step Treatment under hydrogen pressurization | | | Benzene partial hydrogenation reaction Cyclohexene |
|---|---|---|---|---|
| | Temperature (° C.) | Hydrogen partial pressure (MPa) | Total pressure (MPa) | Time (hr) | selectivity at a benzene conversion rate of 50% (%) |
| Example 15 | 200 | 3.50 | 5.05 | 2.0 | 87.6 |
| Comparative Example 13 | 170 | 3.50 | 4.29 | 2.0 | 81.5 |

Modes (Examples) in which an aqueous zinc sulfate solution is added to catalyst slurry tends to have a high cyclohexene selectivity, compared to the Examples in which cobalt sulfate was added (for example, Example 10 and Comparative Example 9). However, if comparison is made between the systems common in metal component (for example, Example 15 and Comparative Example 13), in the case where reduction was made under the conditions of the embodiment and the second step was performed, a cyclohexene selectivity is found to be high.

Reference Example 1

(1) Synthesis of Zirconia Carrier

Hafnium oxide-containing zirconia sol (zirconia (10 mass %) containing liquid, trade name "ZSL-10T" produced by Daiichi Kigenso Kagaku Kogyo Co., Ltd.) (500 g) was gradually added to a 25% ammonia water while stirring under conditions of 40° C. The liquid obtained was stirred while heating at 80° C. for 1 hour, and dried at 90° C. under reduced pressure to obtain a solidified mass of powder. The solidified mass of powder was pulverized, added into a 0.5 N aqueous sodium hydroxide solution, stirred at 60° C. for 1 hour, washed with water, and filtrated. This procedure was repeated five times. The resultant solid substance was sufficiently dried under vacuum at 110° C., and sufficiently calcined at 400° C. to obtain 45 g of white zirconia powder. The specific surface area of the powder was measured by a BET method based on nitrogen adsorption. As a result, it was 109 m$^2$/g.

Examples 16 to 26

(2) Preparation of Zirconia-Supported Ruthenium Catalyst Slurry

To an aqueous solution dissolving lanthanum acetate hydrate (14.8 g), zirconia powder (20 g) obtained as described above was added and mixed by stirring for 1 hour. The resultant mixture was sufficiently dried at 80° C. under reduced pressure to obtain a solid substance, which is then sufficiently calcined at 400° C. In this manner, zirconia powder carrying lanthanum in an amount of 25 mass % in terms of oxide was obtained. Subsequently, to an aqueous ruthenium chloride solution (containing ruthenium (10%))(22 g), water was added to obtain an aqueous solution. To the aqueous solution, the zirconia powder carrying lanthanum was added to support a ruthenium component by adsorption. Thereafter, filtration, washing with water, and alkali treatment performed at 50° C. for 1 hour, filtration and washing with water were sequentially performed. A lanthanum and ruthenium supported on zirconia powder (30 g) thus obtained and a 10 mass % aqueous zinc sulfate solution (280 mL) were placed in an autoclave and stirred under hydrogen and in the conditions of 150° C. and a total pressure of 5.5 MPa (hydrogen partial pressure 5.0 MPa) for 24 hours. In this manner, a reduction treatment was performed to obtain a ruthenium catalyst precursor. When the resultant ruthenium catalyst precursor was analyzed by fluorescent X-rays, ruthenium was contained in an amount of 11 mass % and zinc in an amount of 2.0 mass %. Furthermore, the average crystallite diameter of a ruthenium catalyst was about 3 nm. The resultant ruthenium catalyst precursor (2 g) was added to a 10 mass % aqueous zinc sulfate solution (280 mL) to prepare a catalyst precursor slurry. The catalyst precursor slurry was stirred under hydrogen and in the conditions of 200° C. and a total pressure of 5 MPa (hydrogen partial pressure 3.5 MPa) for 2 hours to prepare a zirconia-supported ruthenium catalyst slurry dispersed in an aqueous zinc sulfate solution.

(Partial Hydrogenation Reaction of Benzene Using Zirconia-Supported Ruthenium Catalyst Slurry in an Aqueous Zinc Sulfate Solution)

The ruthenium catalyst slurry obtained above was directly cooled to a temperature of 140° C. for 15 minutes. To this, benzene (140 mL) was added at a total pressure of 5 MPa to perform a benzene partial hydrogenation reaction. As a result, the cyclohexene selectivity at a benzene conversion rate of 50% was 86.0%.

(Oxygen Treatment and Hydrogen Treatment of Ruthenium Catalyst Slurry)

After the benzene partial hydrogenation reaction, the catalyst slurry was cooled to room temperature, an oil phase was separated and removed by bubbling nitrogen into the catalyst slurry while stirring at 80° C. and bubbling of nitrogen containing 3% oxygen was performed at 80° C. for 5 hours. The catalyst slurry (240 mL) obtained was subjected to hydrogen treatment under hydrogen and in the conditions of various temperatures and pressures shown in Table 8.

(Benzene Partial Hydrogenation Reaction Using Catalyst Slurry Treated with Oxygen and Hydrogen)

The catalyst slurry (240 mL) subjected to the aforementioned treatments was cooled to a temperature of 140° C. after hydrogen treatment. To this, benzene (120 mL) was added at a total pressure of 5 MPa and a benzene partial hydrogenation reaction was performed at 140° C. As a result, the cyclohexene selectivity values at a benzene conversion rate of 50% are shown in Table 8, together with others.

Comparative Examples 14 to 17

In the same manner as in Examples 16 to 26, the ruthenium catalyst precursor (2 g) was added to a 10 mass % aqueous zinc sulfate solution (280 mL) to prepare catalyst precursor slurry. To the ruthenium catalyst precursor slurry, benzene (140 mL) was added at 140° C. and a total pressure of 5 MPa to perform a benzene partial hydrogenation reaction. As a result, the cyclohexene selectivity at a benzene conversion rate of 50% was 79.4%.

From the catalyst precursor slurry subjected to the benzene partial hydrogenation reaction, an oil phase was removed in the same manner as in Examples 16 to 26, and an oxygen treatment was performed. The resultant catalyst slurry (240 mL) was subjected to a hydrogen treatment under hydrogen and in the conditions of various temperatures and pressures shown in Table 8 and benzene (120 mL) was added in the same reaction conditions as in Examples 16 to 26 to perform a benzene partial hydrogenation reaction. The cyclohexene selectivity values at a benzene conversion rate of 50% are collectively shown in Table 8.

TABLE 8

| | Second step Treatment under hydrogen pressurization | | | | Benzene partial hydrogenation reaction Cyclohexene selectivity at a benzene conversion rate of 50% (%) |
|---|---|---|---|---|---|
| | Temperature (° C.) | Hydrogen partial pressure (MPa) | Total pressure (MPa) | Time (hr) | |
| Example 16 | 200 | 3.50 | 5.05 | 1.0 | 86.4 |
| Example 17 | 200 | 1.00 | 2.55 | 1.0 | 85.8 |
| Example 18 | 200 | 5.00 | 6.55 | 1.0 | 85.2 |
| Example 19 | 200 | 0.60 | 2.15 | 2.0 | 85.1 |
| Example 20 | 185 | 1.88 | 3.00 | 1.0 | 85.1 |
| Example 21 | 220 | 3.50 | 5.81 | 1.0 | 85.3 |
| Example 22 | 200 | 3.50 | 5.05 | 4.0 | 86.5 |
| Example 23 | 200 | 3.50 | 5.05 | 2.0 | 86.5 |
| Example 24 | 200 | 3.50 | 5.05 | 0.5 | 85.4 |
| Example 25 | 200 | 3.50 | 5.05 | 10 min | 85.2 |
| Example 26 | 185 | 3.50 | 4.62 | 1.0 | 85.4 |
| Comparative Example 14 | 170 | 3.50 | 4.29 | 1.0 | 79.8 |
| Comparative Example 15 | 230 | 3.50 | 6.29 | 1.0 | 52.1 |
| Comparative Example 16 | 200 | 5.45 | 7.00 | 1.0 | 75.1 |
| Comparative Example 17 | 200 | 0.45 | 2.00 | 1.0 | 74.7 |

Examples 27 to 29

The catalyst slurry (240 mL) of Example 16 treated by bubbling of 3% oxygen-containing nitrogen at 80° C. for 5 hours, was stirred under nitrogen in a closed system at 140° C. for 1 hour. The resultant catalyst slurry (240 mL) was subjected to a hydrogen treatment under hydrogen and in the conditions of various temperatures and pressures shown in Table 9.
(Partial Hydrogenation Reaction Using Catalyst Slurry Subjected to Oxygen Treatment, Heat Treatment Under Nitrogen and Hydrogen Treatment)

The catalyst slurry (240 mL) subjected to the aforementioned treatments was cooled to a temperature of 140° C. after the hydrogen treatment. To this, benzene (120 mL) was added at a total pressure of 5 MPa to perform a benzene partial hydrogenation reaction at 140° C. The cyclohexene selectivity values at a benzene conversion rate of 50% are collectively shown in Table 9.

Comparative Examples 18 to 21

The catalyst slurry (240 mL) subjected to the oxygen treatment of Comparative Example 14 was stirred under nitrogen in a closed system at 140° C. for 1 hour. The resultant catalyst slurry (240 mL) was subjected to a hydrogen treatment under hydrogen and in the conditions of various temperatures and pressures shown in Table 9. Using the catalyst slurry, a benzene partial hydrogenation reaction was performed in the same conditions as in Examples 27 to 29. The cyclohexene selectivity values at a benzene conversion rate of 50% are collectively shown in Table 9.

TABLE 9

| | Second step Treatment under hydrogen pressurization | | | | Benzene partial hydrogenation reaction Cyclohexene selectivity at a benzene conversion rate of 50% (%) |
|---|---|---|---|---|---|
| | Temperature (° C.) | Hydrogen partial pressure (MPa) | Total pressure (MPa) | Time (hr) | |
| Example 27 | 200 | 3.50 | 5.05 | 2.0 | 86.5 |
| Example 28 | 185 | 3.88 | 5.00 | 2.0 | 85.7 |
| Example 29 | 200 | 1.50 | 3.05 | 2.0 | 86.1 |
| Comparative Example 18 | 170 | 4.21 | 5.00 | 2.0 | 79.8 |
| Comparative Example 19 | 230 | 2.21 | 5.00 | 2.0 | 50.1 |
| Comparative Example 20 | 200 | 5.45 | 7.00 | 2.0 | 73.2 |
| Comparative Example 21 | 200 | 0.45 | 2.00 | 2.0 | 72.1 |

Example 30

Using a partial hydrogenation reactor of a known structure having a settling zone capable of separating oil and water within the reactor, a benzene partial hydrogenation reaction was performed in a continuous manner. In the partial hydrogenation reactor, the ruthenium catalyst precursor (15 g) prepared in each of Examples 16 to 26 was added to a 10 mass % aqueous zinc sulfate solution (1200 mL) to prepare catalyst precursor slurry containing the ruthenium catalyst precursor and an aqueous solution of a metal salt. The catalyst precursor slurry was fed to the partial hydrogenation reactor. After the inside of the reactor was sufficiently flushed with hydrogen, the slurry was stirred at 200° C. and a total pressure of 5.1 MPa (hydrogen partial pressure 3.5 MPa) for 4 hours.

Thereafter, the temperature was cooled to 140° C. for 1 hour and a total pressure was regulated to 5 MPa. Then, while high-pressure hydrogen is supplied to the partial hydrogenation reactor, benzene was continuously supplied at a rate of 1.2 kg/h while stirring at a high speed; at the same time, an oil phase generated from the settling zone of the partial hydrogenation reactor was continuously taken out. In this way, cyclohexene was produced in a continuous manner. The reaction temperature was set to 140° C. and the reaction pressure was set to 5.0 MPa in terms of a total pressure. Furthermore, the settling apparatus was controlled such that the ratio of the oil phase to the aqueous phase (catalyst slurry) in the partial hydrogenation reactor becomes ½.

While the benzene partial hydrogenation reaction was performed in a continuous manner, a liquid mixture (720 mL) of an aqueous phase and an oil phase was taken out by way of a cooling pipe from the reactor while stirring every day at the same time. The liquid mixture taken out was subjected to a contact treatment (first step) with oxygen as shown below, and then subjected to a stirring treatment (second step) performed at 200° C. and a total pressure of 5.1 MPa (hydrogen partial pressure 3.5 MPa) to obtain catalyst slurry prepared again. The catalyst slurry reprepared was loaded again to the reactor next day immediately after a liquid mixture (720 mL) was taken out.

(First Step)

A liquid mixture (720 mL) of the aqueous phase and oil phase taken out was separated by settled separation into an oil phase and an aqueous phase. Furthermore, the aqueous phase obtained by separation was heated to 80° C. and bubbled with nitrogen for 1 hour. In this manner, oil was completely removed from the aqueous phase. Thereafter, nitrogen containing 3% oxygen was blown into an aqueous phase of 80° C. under atmospheric pressure while stirring the aqueous phase to perform a treatment of bringing an aqueous phase into contact with oxygen for 5 hours.

(Second Step)

The catalyst slurry obtained through the first step was stirred at 200° C. and a total pressure of 5.1 MPa (hydrogen partial pressure 3.5 MPa) for 1 hour (second step).

The resultant catalyst slurry obtained through the second step was returned to the partial hydrogenation reactor immediately after the liquid mixture was taken out next day.

The oil phase obtained from the settling zone was sampled one hour before the liquid mixture of the aqueous phase and oil phase was taken out every day and analyzed by gas chromatography and reaction results were monitored.

In this manner, a benzene partial hydrogenation reaction was performed in a continuous manner. The reaction results 3000 hours after initiation of the reaction, that is, the benzene conversion rate was 48.2% and the cyclohexene selectivity was 76.1%. By controlling the supply amount of benzene to the reactor, cyclohexene selectivity values at benzene conversion rates of 40%, 50% and 60% were obtained. The results are shown in Table 10.

Furthermore, the continuous reaction was continued up to 6000 hours after initiation of the reaction. The reaction results, that is, the benzene conversion rate was 45.3% and the cyclohexene selectivity was 78.3%. By controlling the supply amount of benzene, cyclohexene selectivity values at benzene conversion rates of 40%, 50% and 60% were obtained. The results are shown in Table 10.

Example 31

In the same manner as in Example 30, the ruthenium catalyst precursor (15 g) prepared in each of Examples 16 to 26 was added to a 10 mass % aqueous zinc sulfate solution (1200 mL) to prepare a catalyst precursor slurry containing a ruthenium catalyst precursor and an aqueous solution of a metal salt.

The benzene partial hydrogenation reaction was continuously performed in substantially the same manner as in Example 30 except that no reduction treatment was applied to the catalyst precursor slurry to manufacture cyclohexene in a continuous manner and the results of the reaction were monitored.

The reaction results 3000 hours after initiation of the reaction, that is, the benzene conversion rate was 48.1% and the cyclohexene selectivity was 75.8%. By controlling the supply amount of benzene to the reactor, cyclohexene selectivity values when a benzene conversion rate was 40%, 50%, 60% were obtained. The results are shown in Table 10.

Furthermore, when a continuous reaction was continued up to 6000 hours after initiation of the reaction, the results of the reaction, that is, the benzene conversion rate was 44.7% and the cyclohexene selectivity was 78.0%. By controlling a benzene supply amount, cyclohexene selectivity values when a benzene conversion rate was 40%, 50%, 60% were obtained. The results are shown in Table 10.

Comparative Example 22

In the same manner as in Example 30, the ruthenium catalyst precursor (15 g) prepared in each of Examples 16 to 26 was added to a 10 mass % aqueous zinc sulfate solution (1200 mL) to prepare a catalyst precursor slurry containing the ruthenium catalyst precursor and an aqueous solution of a metal salt.

The benzene partial hydrogenation reaction was continuously performed in substantially the same manner as in Example 30 except that no reduction treatment was applied to the catalyst precursor slurry to manufacture cyclohexene in a continuous manner.

The first step and second step were as follows. While the benzene partial hydrogenation reaction was performed in a continuous manner, a liquid mixture of an aqueous phase and an oil phase was taken out from a reactor in the same manner as in Example 30. The liquid mixture taken out was subjected to a contact treatment (first step) with oxygen in the same manner as in Example 30 and thereafter subjected to a stirring treatment (second step) performed at 170° C. and a total pressure of 5.0 MPa (hydrogen partial pressure 4.21 MPa) to obtain catalyst slurry reprepared. The catalyst slurry reprepared was loaded again to the reactor next day after a liquid mixture (720 mL) was taken out.

The results of a reaction were monitored in the same manner as in Example 30.

The results of the reaction 3000 hours after initiation of the reaction, that is, the benzene conversion rate was 50.1% and the cyclohexene selectivity was 68.7%. By controlling a benzene supply amount to the reactor, cyclohexene selectivity values when a benzene conversion rate was 40%, 50%, 60% were obtained. The results are shown in Table 10.

Furthermore, when a continuous reaction was continued up to 6000 hours after initiation of the reaction, the results of the reaction, that is, the benzene conversion rate was 49.5% and the cyclohexene selectivity was 67.5%. By controlling a benzene supply amount, cyclohexene selectivity values when a benzene conversion rate was 40%, 50%, 60% were obtained. The results are shown in Table 10.

Comparative Example 23

A continuous reaction was performed in the same manner as in Comparative Example 22 except that the oxygen treatment (first step) of Comparative Example 22 was not performed. As a result, the activity of a ruthenium catalyst reduced with the passage of the reaction time. Accordingly, the benzene conversion rate reduced with the passage of reaction time. The rate became almost zero 980 hours after initiation of the reaction and an operation was not able to be continued.

TABLE 10

|  | Continuous reaction operation time (h) | Cyclohexene selectivity at each benzene conversion rate (%) | | |
|---|---|---|---|---|
|  |  | 40% | 50% | 60% |
| Example 30 | 3000 | 80.5 | 76.5 | 69.1 |
|  | 6000 | 80.6 | 76.7 | 70.0 |
| Example 31 | 3000 | 80.1 | 76.2 | 68.7 |
|  | 6000 | 80.0 | 76.2 | 69.4 |
| Comparative Example 22 | 3000 | 74.2 | 68.9 | 62.0 |
|  | 6000 | 73.5 | 67.3 | 61.1 |

Example 32

Ruthenium chloride ($RuCl_3 \cdot 3H_2O$) (25 g) and zinc chloride (65.0 g) were dissolved in water (2500 mL) while stirring. A 30% aqueous sodium hydroxide solution (350 mL) was added at a time to the aforementioned aqueous solution while stirring. The resultant mixture was stirred further at 80° C. for 2 hours. After cooling, the mixture was allowed to stand still. After the supernatant was removed by decantation, a black precipitate was washed three times with a 1 N aqueous sodium hydroxide solution. In this operation, a black precipitate composed of $Ru(OH)_3$ containing $Zn(OH)_2$ was obtained. To the resultant black precipitate, a 5% aqueous sodium hydroxide solution was added to bring the mixture to a total amount of 2500 mL and reduced under hydrogen pressurization at 150° C. and 5 MPa for 12 hours. After the reaction solution was cooled, the resultant black precipitate was filtrated under an argon atmosphere, and first washed with a 30% aqueous sodium hydroxide solution and then with water. Thereafter, the precipitate was dried under vacuum to obtain 11.3 g of ruthenium catalyst precursor. The ruthenium catalyst precursor had an average crystallite diameter of 5.5 nm and contained zinc in an amount of 7.2 mass %. The resultant ruthenium catalyst precursor (10.0 g) and zirconia ($ZrO_2$) powder (produced by Daiichi Kigenso Kagaku Kogyo Co., Ltd., average particle size 0.35 μm) (50.0 g) were added to a 10 mass % aqueous zinc sulfate solution (1200 mL) to prepare catalyst precursor slurry. The catalyst precursor slurry was stirred under hydrogen and in the conditions of 200° C. and a total pressure of 5 MPa (hydrogen partial pressure 3.5 MPa) for 2 hours to prepare a ruthenium catalyst slurry containing zirconia as a dispersant in an aqueous zinc sulfate solution. The same operation as in Example 30 was performed except that the catalyst slurry was used to continuously perform a benzene partial hydrogenation reaction.

The results of the reaction 3000 hours after initiation of the reaction, that is, the benzene conversion rate was 49.3% and the cyclohexene selectivity was 82.1%. By controlling a benzene supply amount to the reactor, cyclohexene selectivity values when a benzene conversion rate was 40%, 50%, 60% were obtained. The results are shown in Table 11.

Furthermore, when a continuous reaction was continued up to 6000 hours after initiation of the reaction, the results of the reaction, that is, the benzene conversion rate was 48.7% and the cyclohexene selectivity was 82.4%. By controlling a benzene supply amount, cyclohexene selectivity values when a benzene conversion rate was 40%, 50%, 60% were obtained. The results are shown in Table 11.

Example 33

The benzene partial hydrogenation reaction was continuously performed in substantially the same manner as in Example 32 except that no reduction treatment was applied to the catalyst precursor slurry of Example 32, to manufacture cyclohexene in a continuous manner and the results of the reaction were monitored.

The results of the reaction 3000 hours after initiation of the reaction, that is, the benzene conversion rate was 49.5% and the cyclohexene selectivity was 81.5%. By controlling the supply amount of benzene to the reactor, cyclohexene selectivity values when a benzene conversion rate was 40%, 50%, 60% were obtained. The results are shown in Table 10.

Furthermore, when a continuous reaction was continued up to 6000 hours after initiation of the reaction, the results of the reaction, that is, the benzene conversion rate was 48.9% and the cyclohexene selectivity was 81.7%. By controlling a benzene supply amount, cyclohexene selectivity values when a benzene conversion rate was 40%, 50%, 60% were obtained. The results are shown in Table 10.

Comparative Example 24

A continuous reaction was performed in the same method as in Example 32 except that the reduction treatment for catalyst precursor slurry and hydrogen treatment (second step) of Example 32 were not performed. As a result, the results of the reaction 3000 hours after initiation of the reaction, that is, the benzene conversion rate was 49.7% and the cyclohexene selectivity was 70.5%. By controlling a benzene supply amount to the reactor, cyclohexene selectivity values when a benzene conversion rate was 40%, 50%, 60% were obtained. The results are shown in Table 11.

Furthermore, when a continuous reaction was continued up to 6000 hours after initiation of the reaction, the results of the reaction, that is, the benzene conversion rate was 48.4% and the cyclohexene selectivity was 70.1%. By controlling a benzene supply amount to the reactor, cyclohexene selectivity values when a benzene conversion rate was 40%, 50%, 60% were obtained. The results are shown in Table 11.

Comparative Example 25

A continuous reaction was performed in the same method as in Example 32 except that the reduction treatment of catalyst precursor slurry and the oxygen treatment (first step) of Example 32 were not performed. As a result, the activity of a ruthenium catalyst reduced with the passage of the reaction time. Accordingly, the benzene conversion rate reduced with the passage of the reaction time. The rate became almost zero 1020 hours after initiation of the reaction and an operation was not able to be continued.

TABLE 11

|  | Continuous reaction operation time (h) | Cyclohexene selectivity at each benzene conversion rate (%) | | |
|---|---|---|---|---|
|  |  | 40% | 50% | 60% |
| Example 32 | 3000 | 87.2 | 81.8 | 74.1 |
|  | 6000 | 87.4 | 82.3 | 75.4 |
| Example 33 | 3000 | 86.5 | 81.2 | 73.2 |
|  | 6000 | 85.9 | 80.9 | 72.8 |
| Comparative Example 24 | 3000 | 75.3 | 70.3 | 62.0 |
|  | 6000 | 74.6 | 69.2 | 61.1 |

The present application is based on Japanese Patent Application No. 2008-325644 filed on Dec. 22, 2008 with Japanese Patent Office, and the content is incorporated herein by reference.

INDUSTRIAL APPLICABILITY

The present invention has industrial availability as a production method for a cycloolefin. According to the present invention, it is possible that a catalyst maintains high selectivity for a long time. By virtue of this, it is possible to manufacture a cycloolefin stably for a long time while suppressing a decrease of cycloolefin yield.

REFERENCE SIGNS LIST

1 Reactor
2, 32 Heating heater
3, 23, 27 Stirrer
4, 7, 8, 9, 11, 13, 19, 24, 28, 31 Pipe
5, 12, 29 Pump
6 Separator
10 Oil/water separation vessel
14, 30 Hydrogen supply apparatus
15 Benzene supply unit
14A, 15A, 20A, 21A, 30A, 33A Supply nozzle
16 Oil stripping vessel with jacket
17 Oxygen treater with jacket
16A, 17A Heating jacket
18, 25 Condenser
20 Gas supply apparatus
21 Apparatus for supplying gas containing oxygen
22 Pressure drop valve
26 Hydrogen treater
33 Acidic aqueous solution supply apparatus
34 Partition wall
100, 200 Cycloolefin production apparatus

The invention claimed is:

1. A method for preparing a ruthenium catalyst comprising:
    forming a precipitate comprising $Ru(OH)_3$ and $Zn(OH)_2$ from ruthenium chloride and zinc chloride;
    mixing the precipitate with $ZrO_2$ to obtain a ruthenium catalyst precursor containing $ZrO_2$ as a dispersant, wherein the ruthenium catalyst precursor comprises zinc in an amount from 0.1 to 50 parts by mass relative to 100 parts by mass of ruthenium; and
    reducing the ruthenium catalyst precursor in an aqueous solution of zinc sulfate at a temperature within a range of 180° C. to 220° C. and at a hydrogen partial pressure within a range of 1 MPa to 3.5 MPa.

2. A method for producing a cycloolefin, comprising:
    preparing a ruthenium catalyst by the method according to claim 1; and
    partially hydrogenating a monocyclic aromatic hydrocarbon in the presence of said ruthenium catalyst.

3. A method for producing a cycloolefin, comprising:
    producing a cycloolefin by the method according to claim 2;
    separating cycloolefin from an aqueous phase containing the ruthenium catalyst;
    contacting the aqueous phase with oxygen to allow at least part of the ruthenium catalyst into contact with oxygen; and
    reducing at least part of the aqueous phase by holding the aqueous phase at a temperature within a range of 180° C. to 220° C. and at a hydrogen partial pressure within a range of 0.6 MPa to 5 MPa.

* * * * *